United States Patent
Vance

(10) Patent No.: US 10,194,788 B2
(45) Date of Patent: Feb. 5, 2019

(54) OPTICAL SCANNER AND SCANNED LENS OPTICAL PROBE

(71) Applicant: OPTISCAN PTY LTD., Notting Hill (AU)

(72) Inventor: Roderick William Charles Vance, Notting Hill (AU)

(73) Assignee: OPTISCAN PTY LTD., Notting Hill (AU)

(*) Notice: Subject to any disclaimer, the term of this patent is extended or adjusted under 35 U.S.C. 154(b) by 331 days.

(21) Appl. No.: 14/900,068

(22) PCT Filed: Jun. 19, 2014

(86) PCT No.: PCT/AU2014/000634
§ 371 (c)(1),
(2) Date: Dec. 18, 2015

(87) PCT Pub. No.: WO2014/201501
PCT Pub. Date: Dec. 24, 2014

(65) Prior Publication Data
US 2016/0143517 A1   May 26, 2016

(30) Foreign Application Priority Data
Jun. 19, 2013  (AU) ............................. 2013902228

(51) Int. Cl.
*A61B 1/04* (2006.01)
*G02B 21/00* (2006.01)
(Continued)

(52) U.S. Cl.
CPC .......... *A61B 1/043* (2013.01); *A61B 1/00096* (2013.01); *A61B 1/00172* (2013.01);
(Continued)

(58) Field of Classification Search
None
See application file for complete search history.

(56) References Cited

U.S. PATENT DOCUMENTS 7,068,878 B2   6/2006  Crossman-Bosworth et al.
2001/0055462 A1  12/2001  Seibel
(Continued)

OTHER PUBLICATIONS

International Search Report for International Patent Application No. PCT/AU2014/000634, dated Aug. 14, 2014 (3 pages).
(Continued)

*Primary Examiner* — Ryan Lepisto
*Assistant Examiner* — Erin Chiem
(74) *Attorney, Agent, or Firm* — Clark & Elbing LLP

(57) ABSTRACT

A lens group for an endoscope or microscope, comprising one or more lens elements, each of uniform refractive index, adapted to: i) focus, with high wavefront aberration correction, driving or excitation light received from an exit tip of an optical waveguide (such as an optical fiber) located substantially against a proximal surface of the lens group to a point observational field with narrow point spread function beyond a distal surface of the lens group (such as outside an optical window located distally relative to the distal surface); and ii) transmit, with high wavefront aberration correction, fluorescence or reflected return light received by the distal surface from the point observational field (and its neighborhood defined by the fluorescence wavelength point spread function) back to the exit tip of the optical waveguide at the fluorescence wavelength.

19 Claims, 28 Drawing Sheets

(51) Int. Cl.
  *G02B 27/42* (2006.01)
  *G01N 21/64* (2006.01)
  *G02B 26/10* (2006.01)
  *G02B 13/18* (2006.01)
  *G02B 23/24* (2006.01)
  *A61B 1/07* (2006.01)
  *A61B 1/00* (2006.01)

(52) U.S. Cl.
  CPC ............ *A61B 1/00188* (2013.01); *A61B 1/07* (2013.01); *G01N 21/6458* (2013.01); *G02B 13/18* (2013.01); *G02B 21/0076* (2013.01); *G02B 23/2476* (2013.01); *G02B 26/103* (2013.01); *G02B 27/425* (2013.01); *G02B 27/4211* (2013.01); *G02B 27/4216* (2013.01); *G01N 2021/6478* (2013.01)

(56) References Cited

U.S. PATENT DOCUMENTS

2004/0254474 A1 12/2004 Seibel et al.
2009/0023999 A1  1/2009 Mathieu et al.
2013/0120550 A1  5/2013 Chen et al.

OTHER PUBLICATIONS

Extended European Search Report for European Application No. 14813769.1, dated May 19, 2016 (9 pages).

Izeddin et al., "PSF shaping using adaptive optics for three-dimensional single-molecule super-resolution imaging and tracking," Opt Express. 20(5):4957-67 (2012) (12 pages).

Azucena et al., "Adaptive optics widefield microscope corrections using a MEMS DM and Shack-Hartmann wavefront sensor," In MEMS Adaptive Optics V, Proc. of SPIE. 7931:79310J (1-6) (2011).

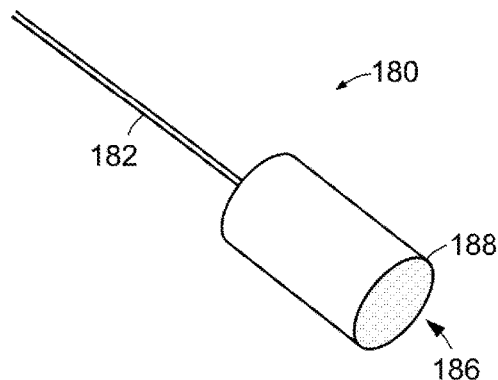
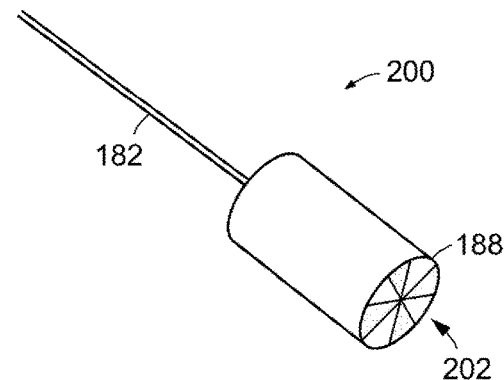
Figure 30A
Figure 30B
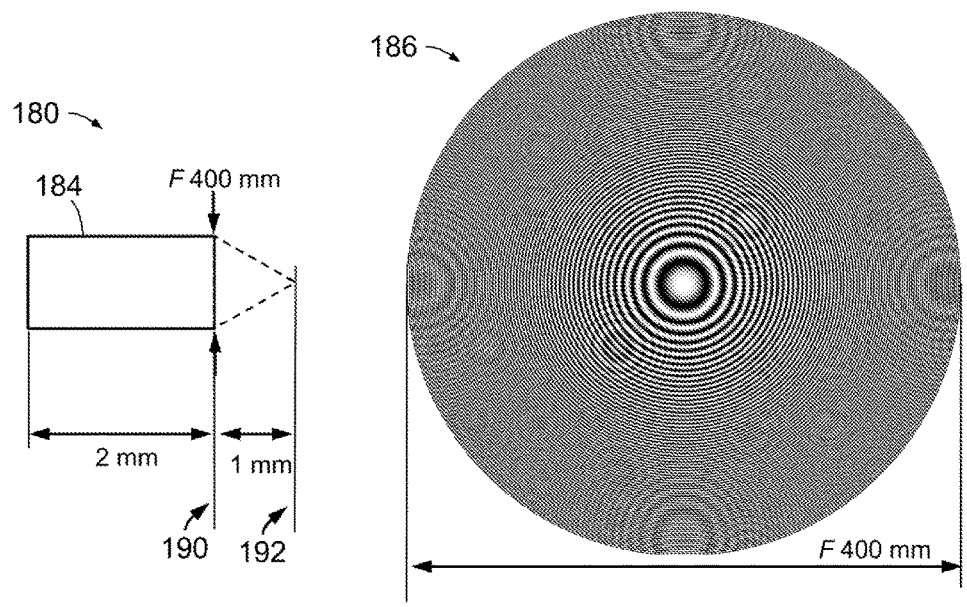
Figure 31

OPTICAL SCANNER AND SCANNED LENS OPTICAL PROBE

FIELD OF THE INVENTION

The present invention relates to a optical scanner and scanned lens optical probe, of particular but by no means exclusive application as a microscope, endoscope or endomicroscope.

BACKGROUND OF THE INVENTION

In general, the further an object is from the centre of an optical system's optical axis, the worse the imaging system's Strehl ratio is and thus the dimmer the object will appear and the worse will be its signal to noise ratio. Moreover, there is a trade-off between field of view and numerical aperture: the higher the numerical aperture of an optical system is (i.e. the smaller the object it can resolve), the smaller is the field of view over which the system's Strehl ratio is acceptably large (particularly for in vivo systems), and over which vignetting is acceptably small. This trade-off arises from the change of the relative geometry of the imaging optics, the object and the object's image as the position of an object changes in the field of view. Practical optical systems that are optimized for on-axis imaging are not simultaneously optimized for off-axis imaging. The higher the system's numerical aperture, the greater the sensitivity of any design to a change in relative geometry between object, imaging system and image. Aberrations, particularly coma, increase off-axis. The focal position at the drive and fluorescence wavelengths must be the same to within the lateral and axial resolutions of the instrument.

For example, FIG. 1 is a schematic view of a many-element confocal collector lens of the background art, with a 0.3 NA, 0.8 Strehl ratio, axial chromatic shift <2 mm and lateral chromatic shift <150 nm over the whole field of view (FOV). In order to manufacture this lens with a Strehl ratio of 0.5 or greater throughout the whole field of view, it is necessary to consider the limitations of existing manufacturing techniques, and the aggregation of manufacturing imperfections, etc., and to take into account the expected radius of curvature of the imaging surface in the tissue (in this example, >3 mm). Hence, a design or theoretical Strehl ratio of 0.95 is required, at both the drive wavelength of 488 nm and fluorescence emission peak wavelength of 532 nm, together with a lateral focal chromatic shift of less than 150 nm and an axial focal chromatic shift of less than 2 μM between the two wavelengths across the whole field of view, all with the radius of curvature of the imaging surface in the tissue being greater than 3 mm. This is achieved by using the multi-element design of lens shown in FIG. 1.

The concatenation of ten optical elements in turn makes it costly to achieve the required stringent optical quality and mechanical tolerances. Assuming that the aberration from imperfections of each surface add incoherently, the aberration of the fourteen air to glass interfaces is roughly $\sqrt{14} \approx 3.7$ times the aberration added by each surface. The required ISO 10110 specifications for each surface within the final assembly is 3/0.5(0.5/−) RMSi <0.05, λ=633 nm and 4/5'.

A further problem with these systems is the low numerical aperture of the output field of the fibre. The numerical aperture (NA) of the field output from a single mode 450 nm fibre is approximately 0.1. For many clinical in vivo imaging applications, numerical apertures of 0.2 or greater are needed. Therefore, optical magnification is needed if a single mode optical fibre's bound eigenfield is to be used as the confocal pinhole to boost this numerical aperture by a factor of two or more. This means that the scanning amplitude of the fibre must be two or more times that of the field of view in the tissue. A scanning system with a magnification of 2× must achieve a scan amplitude of the optical fibre twice that of the wished-for field of view.

A system with a simpler optical arrangement is disclosed in US Patent Application Publication No. 2011/0211104 and further explored in "High-resolution resonant and nonresonant fiber-scanning confocal microscope", J. Biomedical Optics 16(2), 026007 (February 2011). US 2011/0211104 discloses an optical probe for a confocal scanning endoscope. The probe comprises an optical guide, a first lens mounted on a distal end portion of the optical guide for focusing light from the optical guide, an actuator for displacing the distal end portion and the first lens to enable optical scanning, and a second lens inside the probe to receive radiation from the first lens. The second lens, which comprises a negative lens, deflects radiation from the first lens in a direction corresponding to a direction of displacement of the first lens by the actuator. The invention is said to be particularly useful for increasing the field of view (FOV) of cheap, disposable optical probes. Thus, the first lens is mechanically coupled to the optical guide, which avoids the trade-off between field of view and numerical aperture, permitting high values of both parameters, and also eliminates lateral chromatic shift as the relative geometry of the lens, imaged tissue and coverslip stays the same as the on-axis geometry throughout scanning.

However, the system of US 2011/0211104 includes several electrical channels running along a scanning steel tube that couples the first lens to the optical guide, employs large, heavy lenses and does not address the problem of chromatic aberration (other than to calculate the pulse spread for many-photon imaging).

SUMMARY OF THE INVENTION

In a first broad aspect, the present invention provides a lens group for an endoscope or microscope, comprising:
one or more lens elements, each of uniform refractive index, adapted to:
i) focus, with high wavefront aberration correction, driving or excitation light received from an exit tip of an optical waveguide (such as an optical fibre) located substantially against a proximal surface of the lens group to a point observational field with narrow point spread function beyond a distal surface of the lens group (such as outside an optical window located distally relative to the distal surface); and
ii) transmit, with high wavefront aberration correction, fluorescence or reflected return light received by the distal surface from the point observational field (and its neighbourhood defined by the fluorescence wavelength point spread function) back to the exit tip of the optical waveguide at the fluorescence wavelength.

Thus, the lens group breaks down the traditional trade-off between field of view and numerical aperture, as it allows one to have high values of both these parameters, and also allows the minimization or elimination of lateral chromatic shift, by keeping the relative geometry of the lens group, imaged specimen and coverslip the same as the on-axis geometry throughout a scan.

The lens group may be provided in a scanner that is very small and light whilst being highly optically corrected both for aberration and for chromatic shift (either "actively" or "passively", as described below); a bare optical waveguide (e.g. an all glass, conventional optical fibre with no specialised sheathing or other stiffness/inertia modifying device) can be used so that the lens system can be miniaturised enough and scanned at high speed (i.e. at resonant frequencies an order of magnitude faster than the 150 Hz referred to in some of the background art). The lens group may be bonded directly to the (scanning) optical waveguide with essentially no airgap between the optical waveguide and first element of the waveguide, which makes for simplicity in construction and allows active alignment to be readily performed.

The present invention allows the construction of a "Universal" probe that allows simultaneous one-photon and two-photon imaging with effectively any number of fluorophores whilst bringing all wavelengths to the same focus to within 2 µm over a 450 nm to 850 nm spectrum and numerical apertures up to 0.5 NA, and possibly as high as 0.7 NA. Moreover, this chromatic correction provides two-photon imaging performance better than the background art discussed above.

In one embodiment, the fluorescence return light and the driving or excitation light have the same wavelength (i.e. the system is a reflection mode imaging system).

In one embodiment, the lens group further comprises a diffractive optical element bonded to the distal surface. The lens group may comprise a non-focussing glass rod, wherein focussing is provided by the diffractive element.

In another embodiment, the lens group has a chromatic shift that is highly corrected such that the lens group focuses fluorescence light received from the exit tip of the optical waveguide to the point observational field to within a small margin of error (and hence both the driving light and the fluorescence light are focussed to a common point observational field to within that margin of error). In this context, "small margin of error" means small when compared to axial resolution.

In one embodiment, the lens group has a chromatic shift that is highly corrected such that an input light wavepacket of less than a picosecond pulse width and centred at a wavelength of the driving light is only slightly broadened in pulse width when passing through the lens group (so that the loss of peak pulse intensity and two-photon coupling efficiency is small), thus making the system particularly fit for many-photon imaging). For example, a loss of less than 1 dB would be desirable, but a lens group (or system provided therewith) with a 2 dB or a 3 dB loss would also be valuable.

The lens group may have resolution and aberration correction criteria such that:
a) the numerical aperture of light focussed by the lens group is (i) 0.15 or greater when the lens group receives light from the optical waveguide at a nominal driving light wavelength, and (ii) 0.15 or greater at a wavelength of peak fluorescence emission; and
b) either the product of first and second corresponding Strehl ratios measured at the point observational field is either greater than or equal to 0.5 or the generalised Strehl product:

$$\max_{r \in \vec{r}}(\mathcal{S}(r, \lambda_D)^N \times \mathcal{S}(r, \lambda_F)^\alpha)$$ Equation 1 is greater than or equal to 0.5, whichever definition is applicable to a fluorescence imaging mode.

The lens group may have pulse broadening criteria defined such that an input light wavepacket centred at a nominal driving wavelength and of twenty femtoseconds in duration is broadened to a wavepacket at of equal central wavelength and of less than one hundred femtoseconds duration by a multipathing contribution from the lens group.

The lens group may have an outer diameter of less than 1 mm, a length of less than 5 mm and a mass of less than 20 mg.

The lens group may comprise (i) two unlike glasses in the lens group, (ii) a spherical interface between the two unlike glasses, and (iii) a distal surface that is aspheric, whereby the lens group is adapted for driving/fluorescence wavelength pairs in a broadened seeable light spectrum of wavelength 450 nm to 850 nm.

In one embodiment, the lens group comprises one type of glass (and lacks chromatic shift correction devices), wherein the lens group comprises an amount of glass such that transmitted wavefields have insufficient transmit time to disperse to an extent that would produce a Strehl ratio less than 0.5, whereby the lens group is adapted for closely spaced driving/fluorescence wavelength pairs (typically 50 nm apart or less).

The lens group may comprise a plurality of glasses of more than one type, wherein the lens group has mutually cancelling dispersion and the lens group is adapted for use with any driving/fluorescence wavelength pair (including pairs where fluorescence and driving wavelengths are the same) in the broadened seeable light spectrum wavelength range of 450 nm to 850 nm. Two of the glasses may be separated by an intermediate gap (such as an airgap or freespace).

In this embodiment, therefore, the plurality of glasses includes at least two types of glass. Indeed, the plurality of glasses may all be different from one another. Overall, however, they provide mutually cancelling dispersion. In practice, this commonly (but not always) means that the glass order is type A followed by type B (in the proximal group), then type B followed by type A (in the distal group).

In one embodiment, the lens group comprises a homogeneous cylindrical rod and a diffraction grating bonded to the distal end thereof, wherein the grating (rather than a refractive surface) focuses the driving light to the point observational field and guides the return light back from the point observational field into the exit tip of the optical waveguide.

In another embodiment, the lens group comprises a homogeneous cylindrical rod and a diffraction grating bonded to the distal end thereof, wherein the grating (rather than a refractive surface) focuses the driving light to the point observational field, the grating guides the return light back into the exit tip of the optical waveguide, a first portion of the grating is configured for focussing the driving light and a second portion is configured to collecting the return (e.g. fluorescence) light.

In still another embodiment, the lens group comprises a plurality of lens elements (of like or unlike glasses) glued or otherwise bonded together after manufacture, typically by machining. This allows them to be readily built by lens making CNC robots, which otherwise tend to shatter lenses whose side profile is too long and thin.

In a second broad aspect, the present invention provides an optical system, comprising a lens group as described above.

The optical system may comprise the optical waveguide.

In one embodiment, the optical system further comprises a cantilevered mount configured to hold the optical waveguide, a magnet mounted on the optical waveguide, and a drive system for driving the magnet to vibrate in two planes such that the distal surface of the lens groups is scanned at high speed to build up a wide field of view image from the return (e.g. fluorescence) light.

The drive system may be configured to scan in a first direction with a frequency of at least 500 Hz and scan in a second direction orthogonal to the first direction with a frequency of at least 0.5 Hz, such that an image whose field of view is at least 200 µm×200 µm can be obtained from the return (e.g. fluorescence) light.

In a third broad aspect, the present invention provides an optical system, comprising:
an optical waveguide having a main (e.g. single moded) core and a highly multimoded secondary core; and
one or more lens elements, each of uniform refractive index;
wherein an exit tip of the optical waveguide is located substantially against a proximal surface of the lens group;
the main core is configured to transmit driving or excitation light from a light source to the lens group;
the lens group is configured to
  i) focus, with high wavefront aberration correction, the driving or excitation light received from the exit tip of an optical waveguide to a point observational field with narrow point spread function beyond a distal surface of the lens group (such as outside an optical window located distally relative to the distal surface); and
  ii) transmit, with modest aberration correction, fluorescence from the point observational field (and its neighbourhood defined by the fluorescence wavelength point spread function) back to the exit tip of the optical waveguide at the fluorescence wavelength; and
the secondary core is configured to receive the fluorescence.

In one embodiment, the optical system has resolution and aberration correction criteria such that:
a) the numerical aperture of the focussed light is greater than or equal to 0.15 when the optical waveguide is driven at a nominal driving wavelength; and
b) the Strehl product power:

$$\max_{r \in \mathbb{R}^2}(\mathcal{S}(r, \lambda_D)^N) \qquad \text{Equation 2}$$

is greater than or equal to 0.5 for N-photon imaging (i.e. the power N=2 for two-photon imaging, N=3 for three photon imaging, etc).

In the optical system of the second and third aspects, the optical waveguide may further comprise one or more auxiliary lightguiding cores, so that the imaging numerical aperture can be switched between the main, high resolution value to a low value (say 0.1 NA), possibly with in-between steps to allow the user to position the image easily, with coarse axial resolution and high tolerance to siting errors and hand unsteadiness and then switch to a high resolution mode (with lower tolerance) once the target tissue has been identified.

In the optical system of the second and third aspects, the optical waveguide may further comprise one or more axially and sideways offset auxiliary lightguiding cores for selectively receiving the return light from different imaging depths.

In one embodiment, the optical system comprises a quasi-ellipsoidal optical window with a surface shape selected to be parallel to a scanning surface of an apex of the lens group, whereby a relative geometry of the lens group, an instantaneously optically active region of the optical window and the point observational field on a distal side of the optical window remains invariant throughout an image acquisition portion of a scan.

In a fourth broad aspect, the present invention provides an active alignment method, comprising:
mounting an optical waveguide and a lens group as described above comprising a plurality of lens elements in an alignment jig with an exit tip of the optical waveguide substantially against a proximal surface of the lens group
optically driving the optical waveguide;
directing output light from the lens group into an optical detector (such as a wavefront sensor, astronomer's star test apparatus or interferometer);
establishing a least-aberration optimal relative position and orientation by adjusting relative position and orientation of the lens group and the optical waveguide;
bonding the lens elements or otherwise assembling them into fixed relative position and orientation.

In a fifth broad aspect, the present invention provides an lens surface quality assessment method, comprising:
positioning a known diameter pinhole at a focus of an optical system as described above;
optically driving the optical waveguide;
measuring a power transmitted through the pinhole;
removing the pinhole and measuring a total output power; and
determining a measure of a root mean square surface roughness of the lens from a ratio of the power through pinhole to the total power.

In a sixth broad aspect, the present invention provides an in-vivo, one or many-photon descanned fluorescence imaging system comprising the optical system as described above.

It should be noted that any of the various individual features of each of the above aspects of the invention, and any of the various individual features of the embodiments described herein including in the claims, can be combined as suitable and desired.

BRIEF DESCRIPTION OF THE DRAWING

In order that the invention may be more clearly ascertained, embodiments will now be described, by way of example, with reference to the accompanying drawing, in which:

FIGS. 30A and 30B are a schematic view of optical systems with a holographic (grating) lens on a scanned cylindrical substrate according to embodiments of the present invention;

FIG. 31 is a schematic view of the optical system and of the 0.2 NA, 1 mm working distance diffractive lens of FIG. 30A;

DETAILED DESCRIPTION

According to a first group of embodiments of the present invention, there are provided optical systems suitable for a wide range of driving/fluorescence wavelength pairs in the broadened seeable light spectrum of 450 nm to 850 nm wavelength, comprising (i) a lens group of two unlike glasses, (ii) a spherical interface therebetween, and (iii) an aspheric surface on the lens group's distal or output surface.

Figure 2A:
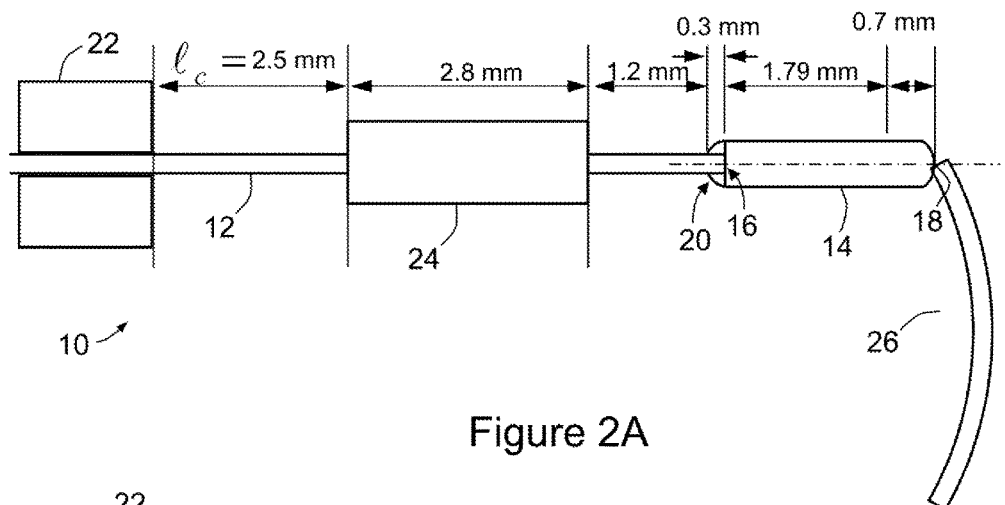
FIGS. 2A and 2B are schematic views of a scanner according to an embodiment of the present invention.
Figure 2B:
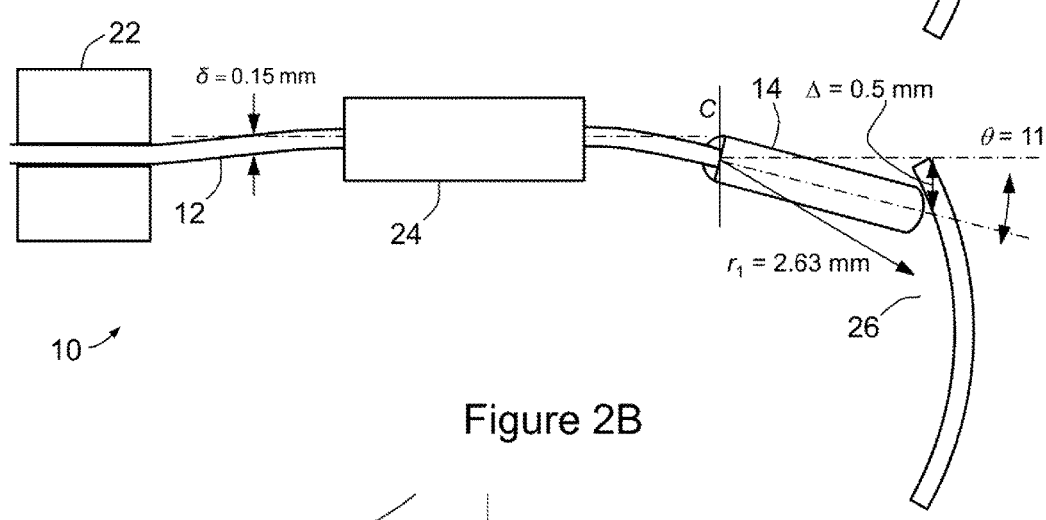

FIGS. 2A and 2B are schematic views of an optical system 10 according to an embodiment of this first group. Referring to FIG. 2A, which depicts optical system 10 at rest, optical system 10 includes a scanning optical fibre 12 and a lens group 14 coupled to the distal tip 16 of optical fibre 12. In this embodiment, optical fibre 12 is in the form of a single mode 450 nm silica optical fibre with a diameter of 125 μm. Lens group 14 is generally cylindrical with a diameter of 250 μm and a length of 2.49 mm. The proximal 1.79 mm of lens group 14 acts as a substrate and comprises N-SF66 glass, while the distal or forward 0.7 mm of lens group 14 comprises an aspheric lens 18 of L-LAM60 glass (described in greater detail below). Lens group 14 comprises two different glasses: in this example, the substrate comprises N-SF66 glass, while aspheric lens 18 comprises L-LAM60 glass. The interface between the two components of lens group 14 is spherical, and the forward or distal face of aspheric lens 18 is aspheric.

A collar 20 is provided on the proximal or rearward end of lens group 14 to securely connect lens group 14 and optical fibre 12; collar 20 generally comprises a meniscus of glue, but may comprise any other material suitable for performing this function and compatible with the intended application of optical system 10. Alternatively, collar 20 may be integral with lens group 14.

Scanner 12 also includes a mount 22 in the form of a cantilever bearing, such as of the type shown in FIG. 2A of U.S. Pat. No. 7,920,312 (which is incorporated herein by reference), in which optical fibre 12 is held, and a magnet 24 for use in driving the scanner, mounted on optical fibre 12 between mount 22 and lens group 14. In this embodiment, magnet 24 is a samarium cobalt magnet with a square cross section of 700 μm×700 μm, and a nominal average density of 7083 kg·m$^{-3}$ to account for the bore or slot cut in it to accommodate optical fibre 12.

In use, optical system 10 would generally be housed within, for example, an endoscope head, which would desirably include an optical window; in this embodiment, this optical window is in the form of an ellipsoidal window or coverslip 26 that both accommodates the motion of aspheric lens 18 and, being ellipsoidal, reduces optical distortion that might otherwise be introduced by the window, and thereby maintain the optical performance across the whole field of view when the scan surface curvature and/or scanner numerical aperture is high. Window 26 is of N-BK7 in this and the other embodiments described below, which also has good biocompatibility.

FIG. 2B depicts optical system 10 in use, illustrating the bending or displacement of its components when aspheric lens 18 is at one extreme of a 0.5 mm amplitude scan when optical system 10 is employed in first overtone vibration mode. To achieve such a scanning motion, magnet 24 is driven so as to execute a side-to-side translation (without rotation) of 0.15 mm. This mode's resonant frequency is 1617 Hz. A suitable driving mechanism is disclosed in U.S. Pat. No. 7,920,312, comprising a pair of Y drive coils disposed above and below magnet 24 (to execute a non-resonant linear Y scan: cf. coils 54a and 54b of FIG. 3 of U.S. Pat. No. 7,920,312) and a pair of X drive coils disposed on either side of magnet 24 (to execute a resonant sinusoidal X scan: cf. coils 56a and 56b of FIG. 3 of U.S. Pat. No. 7,920,312).

It is expected that about 70% of the field of view will be used when optical system 10 builds a raster-scanned image up, the rest being the wend-back part of the sinusoidal scan and therefore badly distorted owing to the lens tip's deceleration to switch direction). Optical system 10 has an approximately 700 μm×700 μm field of view.

The scan surface curvature of this example is high, with the fast, resonant X scan radius of curvature being 2.6 mm. The principle curvature in the orthogonal or Y (nonresonant, slow scan) direction is 8.2 mm. Even so, with this high curvature, the scanning surface deviates from flatness only 24 μm over the whole 700 μm×700 μm field of view. Lower frequency, longer systems are possible with correspondingly longer radii of curvature, according to other embodiment of the present invention.

Figure 4:
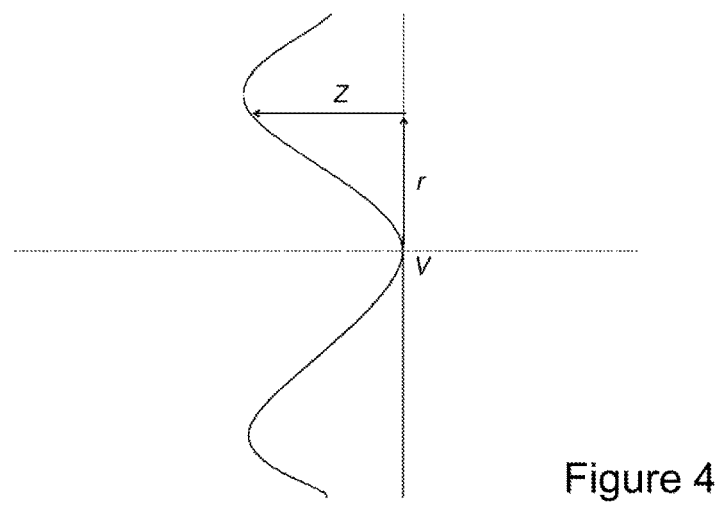
FIG. 4 is a graphical representation of the definition of an aspheric surface.
Figure 3:
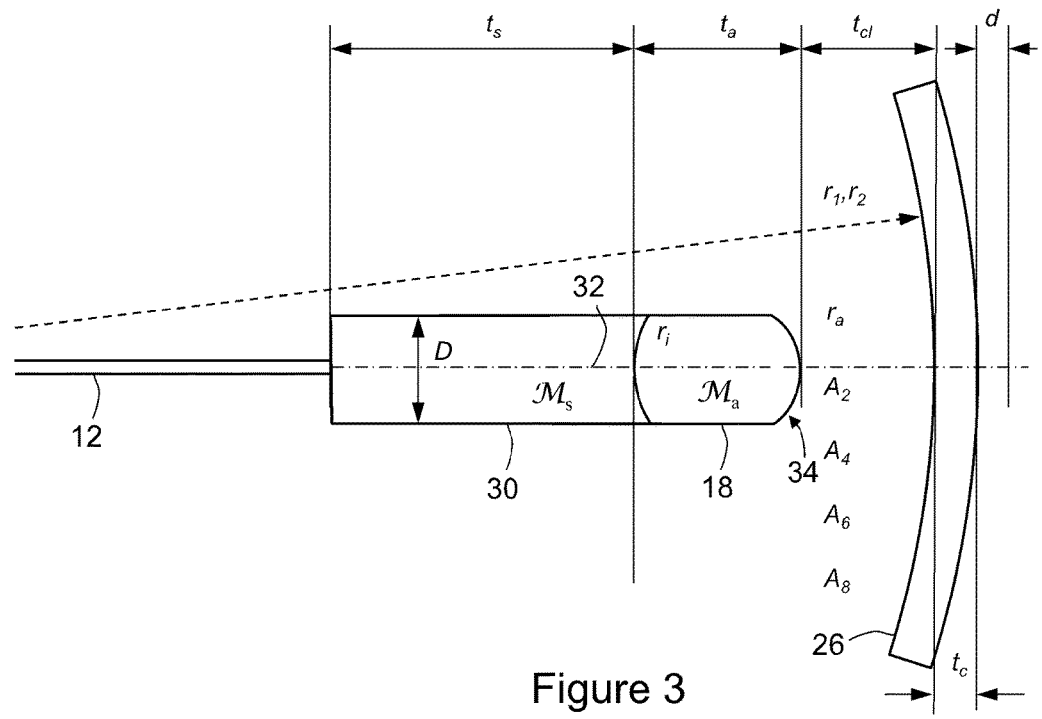
FIG. 3 is a more detailed schematic view of the lens group of the scanner of FIGS. 2A and 2B.

FIG. 3 is a more detailed schematic view of lens group 14 and its coupling to optical fibre 12 (though omitting collar 20 for simplicity). As described above, lens group 14 comprises a proximal substrate 30 of N-SF66 glass and distal aspheric lens 18 of L-LAM60 glass, both with resting optical axis 32. Lens group 14 is adapted for imaging in the wavelength range 450 nm to 850 nm. FIG. 4 is a graphical representation of the definition of an aspheric surface.

In an alternative embodiment, optical system 10 is adapted for use as a fluorescence scanner, and is adapted for closely spaced driving/fluorescence wavelength pairs (typically 50 nm apart or less). Lens group 14 in this alternative embodiment comprises only one type of glass and chromatic shift correction devices are omitted; instead chromatic shift performance is achieved by employing a very small amount of glass, to deny transmitted light enough time in their flight to disperse enough to thwart the reaching of the Strehl ratio product goal described below.

The aspherical forward surface 34 of aspheric lens 18 is nominally axisymmetric (i.e. has rotational symmetry about the optical axis) and is specified by the standard functional form:

$$z = \frac{r_a}{r_a - \sqrt{r_a^2 - r^2}} + A_2 r^2 + A_4 r^4 + A_6 r^6 + A_8 r^8 \qquad \text{Equation 3}$$

where z (see FIG. 4) is the "sag" of the surface measured relative to the plane orthogonal to the optical axis through the vertex V (viz. where the surface meets the optical axis) as a function of the orthogonal distance r from the optical axis. In the example of FIG. 4, z is negative. (z is positive if the surface at the point in question lies to the right of the vertex V.)

The parameters of various embodiment (including that of FIGS. 2A to 3) are presented in Table 1. These examples are designed for different tasks and different degrees of difficulty in building them are foreseen. The examples are not exhaustive and are a sample of what may be realistically be achieved with an aspheric lens and one substrate that meet in a plane or spherical interface. Higher degrees of correction can be obtained, in other embodiments, by using several substrates of different glass with spherical or aspherical interfaces in combination with an aspheric distal surface such as that shown in FIGS. 2A to 3, but these gains are expected to be small.

Commercially available single mode fibre at 488 nm wavelength is assumed for calculating the main numerical aperture of each example. This fibre has a Petermann II mode field diameter of 3.4 μm and a Petermann II output numerical aperture of 0.095 (even though its multimode, "material" numerical aperture is quoted to be 0.12).

Figure 5:
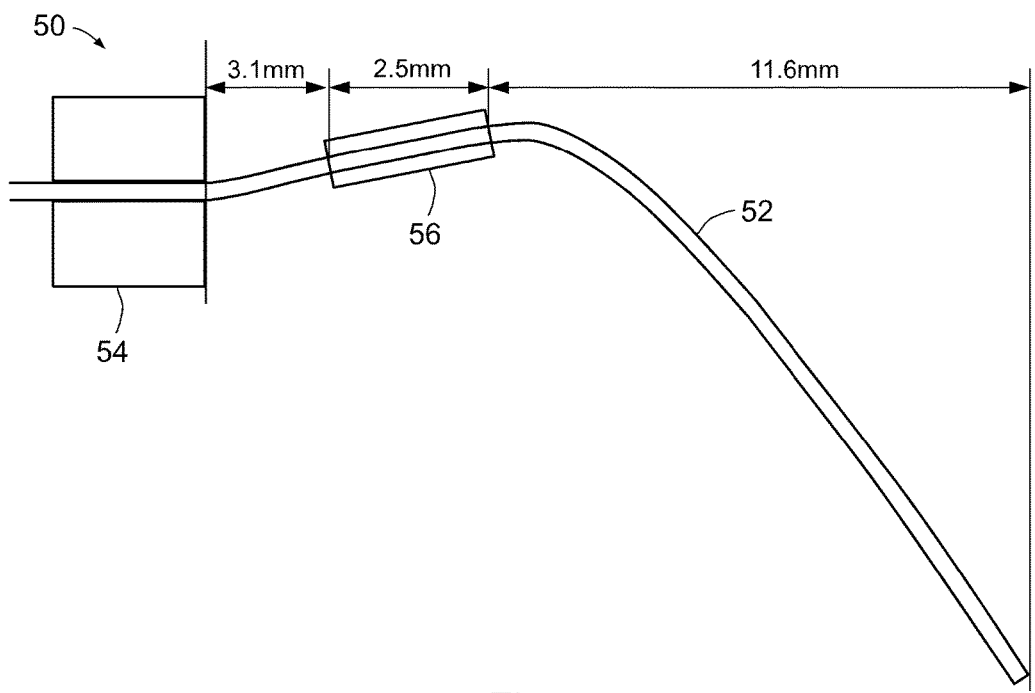
FIG. 5 is a schematic view of a 'datum system' omitting the lens group.

The exemplary lenses detailed in Table 1 are designed to accommodate higher numerical aperture, specialist fibres if these are available and desired. Thus, for example, the first system ("Uncorrected 0.40/0.26 NA") will achieve 0.26 NA with current SM450 fibre, but it is designed to correct an input field of up to 0.15 NA, as shown in the row "Fibre Output Petermann II Mode Field Diameter at $\lambda_D$" by the two figures 0.095 (0.15). If this latter numerical aperture is achieved with a specialist fibre (e.g. in "holey fibre" technology), the bracketed numerical aperture of 0.4 NA with Strehl ratios comparable to that listed at the bottom of the column for this design can be foreseen. Likewise, the design "Universal 0.50/0.33 NA" achieves 0.50 NA with current single mode fibre, but the design itself can accommodate an input numerical aperture of up to 0.15, when its output numerical aperture would be 0.50 whilst achieving the same Strehl ratios as listed in the bottom of the column for that design.

rotate at the first overtone resonance. The corresponding performance parameters for a "datum" system 50 illustrated schematically in FIG. 5 are given in the last column: these parameters relate to a bare fibre without a scanned lens, to give a rough guide to the difficulty of achieving the parameters for the other scanners of Table 1. For example, the row "Driving Force Amplitude for Slow Scan Direction" shows

TABLE 1

Parameters of Refractive Scanners and Optical Performance

| Parameter Name | Symbol (cf. FIG. 3) | Uncorrected 0.40/0.26 NA | 0.47/0.30 NA | Universal 0.50/0.33 NA |
|---|---|---|---|---|
| Substrate thickness | $t_s$ (mm) | 1.795882 | 1.611574 | 2.091975 |
| Substrate material | $M_s$ | N-SF66 | S-NPH2 | S-NPH2 |
| Substrate interface radius (shown negative in FIG. 3) | $r_i$ (mm) | ∞ (flat) | ∞ (flat) | +0.446065 |
| Aspheric lens thickness | $t_a$ (mm) | 0.7 | 0.688937 | 0.727895 |
| Aspheric lens material | $M_A$ | L-LAM60 | L-LAM60 | L-LAM60 |
| Aspheric lens radius | $r_a$ (mm) | −8.720051 | −0.259212 | +0.354615 |
| Aspheric quadratic coefficient | $A_2$ (mm$^{-1}$) | −1.856099 | −0.425953 | −3.403506 |
| Aspheric lens quartic coefficient | $A_4$ (mm$^{-3}$) | +6.188813 | +21.317379 | +3.176098 |
| Aspheric lens sextic coefficient | $A_6$ (mm$^{-5}$) | −37.742987 | −162.135748 | −46.765445 |
| Aspheric lens octic coefficient | $A_8$ (mm$^{-7}$) | 0 | +3157.445438 | 0 |
| Lens-window resting clearance | $t_{cl}$ (mm) | 0.2 | 0.2 | 0.2 |
| Window thickness | $t_c$ (mm) | 0.3 | 0.2 | 0.3 |
| Nominal imaging depth | d (mm) | 0.099 | 0.05 | 0.1 |
| Ellipsoidal window principal curvature radii | $r_1, r_2$ (mm) | 2.83, 8.44 | 2.76, 8.19 | 2.69, 9.08 |
| System drive wavelength | $\lambda_D$ (nm) | 488 | 488 | >450 |
| System fluorescent wavelength | $\lambda_F$ (nm) | 532 | 532 | <850 |
| Fibre output Petermann II mode field diameter at $\lambda_D$ | $d_{P2}$ (μm) | 3.4 (2.2) | 3.4 (2.2) | 3.4 (2.2) |
| Fibre output Petermann II numerical aperture at $\lambda_D$ | $\eta_{P2}$ | 0.095 (0.15) | 0.095 (0.15) | 0.095 (0.15) |
| Scanned lens diameter | D (mm) | 0.5 | 0.5 | 0.6 |
| System output numerical aperture (Petermann II) | $\eta_{out}$ | 0.26 (0.40) | 0.30 (0.47) | 0.33 (0.50) |
| Petermann II system lateral resolution | $\Delta x_{FWHM}$ (μm) | 0.76 | 0.66 | 0.63 |
| System axial resolution (FWHM) | $\Delta z_{FWHM}$ (μm) | 9.6 | 7.25 | 7.0 |
| Strehl ratio at $\lambda_D$ | $S_D$ | 0.98 (0.93) | 0.97 (0.89) | 0.96 (0.96) |
| Strehl ratio at $\lambda_F$ | $S_F$ | 0.96 (0.92) | 0.97 (0.84) | 0.96 (0.96) |
| Vignetting loss (one pass)[1] | $L_V$ (dB) | 0.7 | 0.65 | 0.9 |
| Reflection loss (one pass)[2] | $L_R$ (dB) | 0.4 | 0.35 | 0.4 |
| Photon no. (fluorescence confocal microscopy)[3] | N | 1400 | 2350 | 3400 |

[1] At 488 nm wavelength; the full, there-and-back loss in fluorescence one photon microscopy e.g. with FITC (fluorescein) is roughly twice this value.
[2] At 488 nm wavelength; the full, there-and-back loss in fluorescence one photon microscopy e.g. with FITC (fluorescein) is roughly twice this value.
[3] Total number of returned photons gathered by one-photon fluorescence microscopy imaging of subresolvable fluorophore containing 105 fluorescein ions with 100 μW of 488 nm driving light in the 0.095 NA SM450 optical fibre and 300 ns dwell (i.e. photon gathering) time Scanner performances are assessed by the theoretical performance parameters in Table 1. It should be noted that the Strehl ratios are not the peak Strehl ratios at the wavelength, but rather those defined below, that is, the Strehl Ratios at a focus defined as that point which maximises the product of the two Strehl ratios at driving and fluorescence wavelength.

Table 2 presents the mechanical performance parameters for scanners of Table 1. The scanners' mechanical performance has been set by adjusting the length $l_c$ (see FIGS. 2A and 2B) of the fibre between the cantilever bearing and the nearest edge of the scanning magnet so that the scanning magnet undergoes pure side to side translation and does not that the system scanning the "Universal 0.50/0.33 NA" lens group will need a slow scan driving force that is 485/200=2.4 times as strong as that of the datum system. Apart from the omission of a distal lens group, datum system 50 is similar to optical system 10 of FIGS. 2A and 2B, and has an optical fibre 52 is in the form of a single mode 450 nm silica optical fibre with a diameter of 125 μm, a mount 54 in the form of a cantilever bearing in which optical fibre 52 is held, and a magnet 56 for use in driving optical fibre 52, mounted on optical fibre 52 between mount 22. Magnet 56 is a samarium cobalt magnet with a square cross section of 550 μm×550 μm.

TABLE 2

Mechanical Performance Parameters for Scanned Systems at 1 mm Amplitude Scan

| Mechanical Performance Parameter | Symbols (FIGS. 2A, 2B & 3) | Uncorrected | | Universal | Datum |
|---|---|---|---|---|---|
| | | 0.40/0.26 NA | 0.47/0.30 NA | 0.50 0.33 NA | |
| Ellipsoidal window inside principal curvature radii | $r_1, r_2$ (mm) | 2.83, 8.44 | 2.76, 8.19 | 2.69, 9.08 | N/A |
| Bearing to magnet fibre span | $l_C$ (mm) | 2.5 | 2.4 | 3.0 | N/A |
| Fast scan resonant frequency | $f_{res}$ (kHz) | 1.617 | 1.753 | 1.267 | 0.8734 |
| Driving force amplitude for fast scan direction | $F_{fast}$ (μN) | 452 | 528 | 295 | 161 |
| Sideways magnet displacement amplitude for fast scan direction | $\delta_{fast}$ (μm) | 290 | 270 | 400 | 97 |
| Driving force amplitude for slow scan direction | $F_{slow}$ (mN) | 15.9 | 17.5 | 11.2 | 5.85 |
| Sideways magnet displacement amplitude for slow scan direction | $\delta_{slow}$ (μm) | 485 | 495 | 485 | 200 |

Example 1: Chromatically Uncorrected 0.26 NA System "Uncorrected 0.40/0.26 NA"

Figure 1:
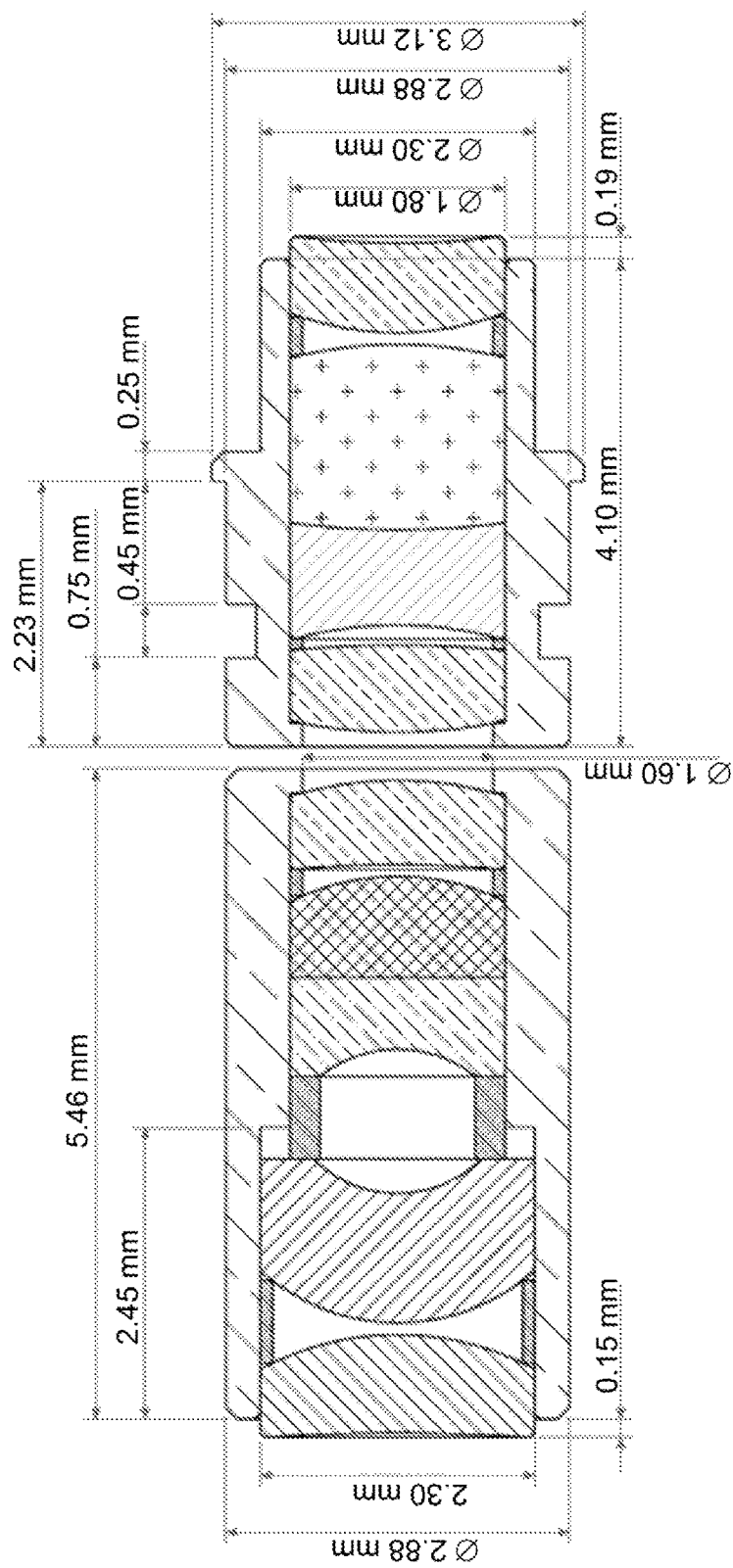
FIG. 1 is a schematic view of a many-element confocal collector lens of the background art.
Figure 6:
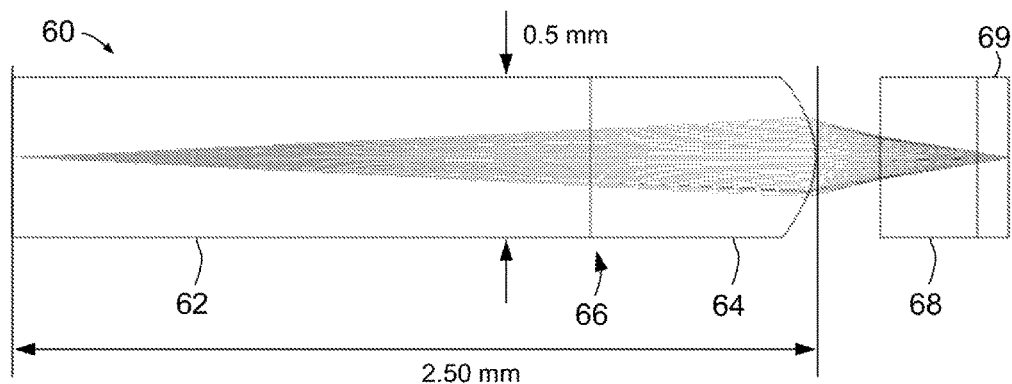
FIG. 6 is a schematic view of a 0.26 NA Uncorrected System with rays for a 0.095 NA input from lightguide according to an embodiment of the present invention.

FIG. 6 is a schematic view of a lens group 60 suitable for use in a scanner such as optical system 10, shown with a window or coverslip 68, a tissue specimen 69 and rays for a 0.095 NA input from a lightguide. This design assumes that the focus is 50 or 99 μm deep into specimen 69 (see "Nominal imaging depth" in Table 1). Lens group 60 constitutes an 0.26 NA uncorrected system, and is adapted for FITC (fluorescein isothiocyanate) one photon fluorescence confocal imaging with FITC as the fluorophore; hence, the driving wavelength is 488 nm and the fluorescence returns in a band stretching from roughly 520 nm to 550 nm with a 532 nm fluorescence peak wavelength. The optical performance is designed to be slightly better than that of a bulk optic system of the type shown in FIG. 1. Lens group 60 has a substrate 62 of Schott (trade mark) N-SF66 and the aspheric lens 64 of Ohara (trade mark) L-LAM60, which meet at a panar interface 66. The former lets planar interface 66 be partly chromatic correcting, the latter (as discussed below) is near to a least nett dispersion glass for the application.

Example 2: Chromatically Uncorrected 0.30 NA System "Uncorrected 0.47/0.30NA"

Figure 7:
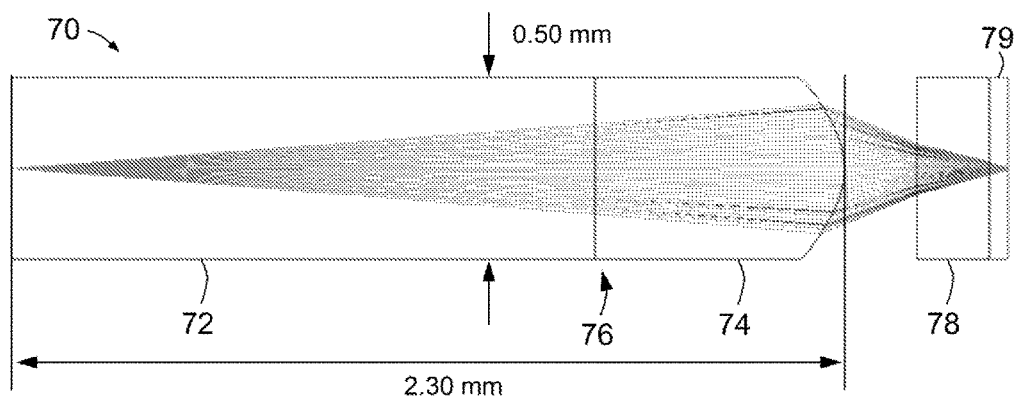
FIG. 7 is a schematic view of Profile for 0.30 NA Uncorrected System "Uncorrected 0.47/0.30NA" according to an embodiment of the present invention.

FIG. 7 is a schematic view of a lens group 70, shown with a window or coverslip 78 and a tissue specimen 79. This example is also suitable for use in a scanner such as optical system 10, being adapted for FITC one photon fluorescence confocal imaging but with optical performance significantly better than that of the bulk optic system of FIG. 1. Its shorter length and higher magnification makes it slightly more sensitive to manufacturing imperfections (discussed below). Lens group 70 comprises a substrate 72 of Ohara S-NPH2 and an aspheric lens 74 of Schott L-LAM60; substrate 72 of Ohara S-NPH2 yields slightly better partial chromatic correction at the higher numerical aperture.

This numerical aperture is approximately the highest that is worth striving for with an uncorrected system of this sort, because the axial responses (i.e. the maximum intensity of the focussing light in a given plane of constant axial position as a function of the axial position of that plane) at the drive and fluorescence wavelengths have peaks that are axially shifted from one another by about 5 μm for a lens group of the rough size of the two uncorrected systems shown. This shift is roughly independent of design (when restricted to embodiments according to claim 0) and numerical aperture. This design in principle needs no correction. Lens group 70 is in two pieces (i.e. substrate 72 and aspheric lens 74) only for production purposes, as it would be very difficult to machine a long thin element integrally without shattering it. Hence, lens group 70 is, in this example, made in two pieces that are then glued together. However, given that two pieces of glass are to be used for manufacturing convenience, it becomes possible to employ two types of similar glass to obtain a small amount of correction from flat interface 76. The difference in performance between this device and one made of one glass (whether in two pieces of one) is very small, however, so this example is described as "uncorrected": the small correction is not essential and is minor compared with that of so-called "corrected" designs described below (see, for example, Example 3).

At low numerical apertures, the wide axial spread of the axial responses means that drive and fluorescence responses almost wholly overlap, even notwithstanding the shift and thus the maximum product of the drive and fluorescence Strehl ratios is not to different from the product of maximum Strehl ratios. However, as numerical aperture rises, so too does the significance of the shift and the peaks in the two axial responses become more starkly resolved, thus the maximum Strehl product is much less than one even though the maximum Strehl ratios for each wavelength are very high. In short, the significance of axial chromatic shift rises with rising numerical aperture, and thus chromatic correction is needed to reap the benefit of greater numerical aperture.

Example 3: Fully Chromatically Corrected 0.33 NA System "Universal 0.50/0.33NA"

Figure 8:
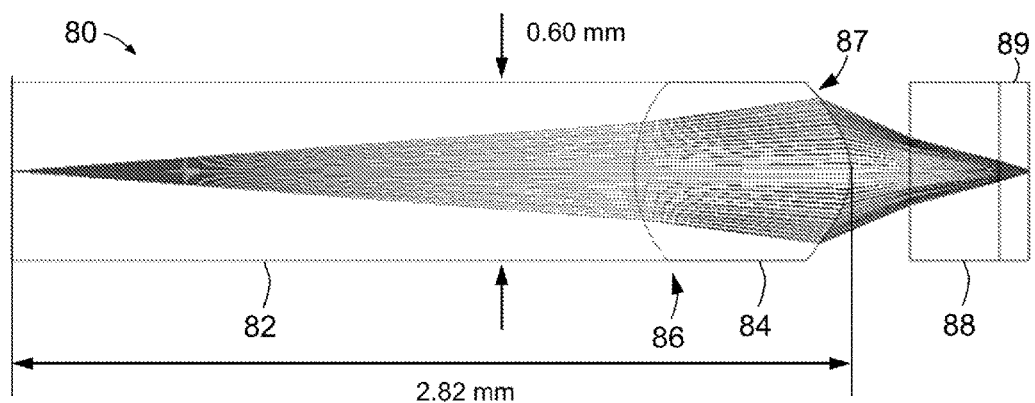
FIG. 8 is a schematic view of Profile for 0.33 NA Universal System "Universal 0.50/0.33NA" according to an embodiment of the present invention.

FIG. 8 is a schematic view of a lens group 80, shown with a window or coverslip 88 and a tissue specimen 89. This example is also suitable for use in a scanner such as optical system 10, and comprises a substrate 82 of Ohara S-NPH2 and an aspheric lens 84 Ohara L-LAM60, which meet at a spherical interface 86. Lens group 80 is adapted to transmit light at wavelengths between 450 nm and 850 nm to essentially the same focus, to within a micron, owing to the opposite wavelength variations for the optical powers from spherical interface 86 on the one hand and the aspherical interface 87 between the Ohara L-LAM60 glass of aspheric lens 84 and freespace at the distal tip of lens group 80.

As a result, lens group 80 can be used for a variety of many-channel one-photon or two photon fluorescence/reflection confocal microscopy or endoscopy systems. Arbitrarily many drive wavelengths in the band 450 nm to 850 nm can be used; these are brought to a common focus, which is also the point of greatest coupling probability back into an optical fibre (cf. optical fibre 12 of FIGS. 2A to 3) through lens group 80 for any fluorescence/reflection in the band. Some more detailed analyses in § 0 back these statements up and show how widely applicable the scanning fully chromatically corrected lens group of claim 0 is. No confocal or two photon system available at the time of writing (2012) has all these capabilities, especially over the whole and very wide fields of view (up to 1 mm×1 mm) foreseen for these systems.

More generally, the preferred materials for aspheric lens 14, for most applications, are found to be in the middle of the Abbe chart. Low refractive index, low dispersion materials, so called "Crown Glasses" (e.g. N-FK51A), need very severe aspheric surfaces for a given optical power, thus the surface itself becomes dispersive even though the material is not. At the other end of the Abbe chart, high refractive index highly dispersive materials, so called "Flint Glasses" (e.g. N-SF66), are highly dispersive, but one only needs relatively mild aspheric surfaces to attain the same optical power. The middle of the Abbe Chart, such as L-LAM60, is the best compromise: aspherical surfaces are mild and the material itself less dispersive than the high refractive index materials like N-SF66 or S-NPH2.

An exception to this principle is diamond, which has very low dispersion (roughly that of N-BK7) and a refractive index of 2.4. This may be the optimal material for uncorrected systems, provided a suitable machining method is used to manufacture good quality aspheric surfaces. It is foreseen to be a key material for use in embodiments of the present invention in the future, when machining methods, e.g. electron beam lathing of chemical vapour deposition (CVD)-grown diamond aspherical lenses, become more viable.

In some embodiments, a scanner is provided with a lens group that comprises more than two optical elements (such as for use in very high numerical aperture devices). However, the two element configuration of lens group 14 of FIGS. 2A to 3 permits, for numerical apertures up to about 0.6, the focussing, with high wavefront aberration correction, of excitation light at the output of optical fibre 12 to a high-resolution (narrow point spread function) point outside ellipsoidal window 26, and the transmission, also with high wavefront aberration correction, of fluorescence and/or reflected light from the same point (and its neighbourhood defined by the fluorescence wavelength point spread function) back to the output of optical fibre 12 at the fluorescence wavelength. This configuration also has the following special geometrical and manufacturing properties:

i) One potential manufacturing imperfection is misalignment between the two elements of lens group 14 is reduced to a pure rotation (say, by an angle $\delta\theta$) of substrate 30 relative to aspheric element 18, owing to the fact that the interface between substrate 30 relative to aspheric element 18 is spherical and can thus be almost wholly cancelled in active alignment by shifting point of attachment of optical fibre 12 to substrate 30 sideways by a compensating offset;

ii) Another potential manufacturing imperfection is the decentring of the spherical surface (that constitutes the interface between substrate 30 and aspheric element 18) but its effect can also be cancelled by a compensating sideways offset of the point of attachment of optical fibre 12 to substrate 30;

iii) Long, thin lenses are not readily manipulated and machined by CNC (computer numerical control) lens building robots without a high risk of shivering, so even a one-element design is best made of two sections of the same material, with a plane interface between them. One may take advantage of the manufacturing constraint by employing different materials on either side of the interface to provide partial chromatic correction.

Figure 9:
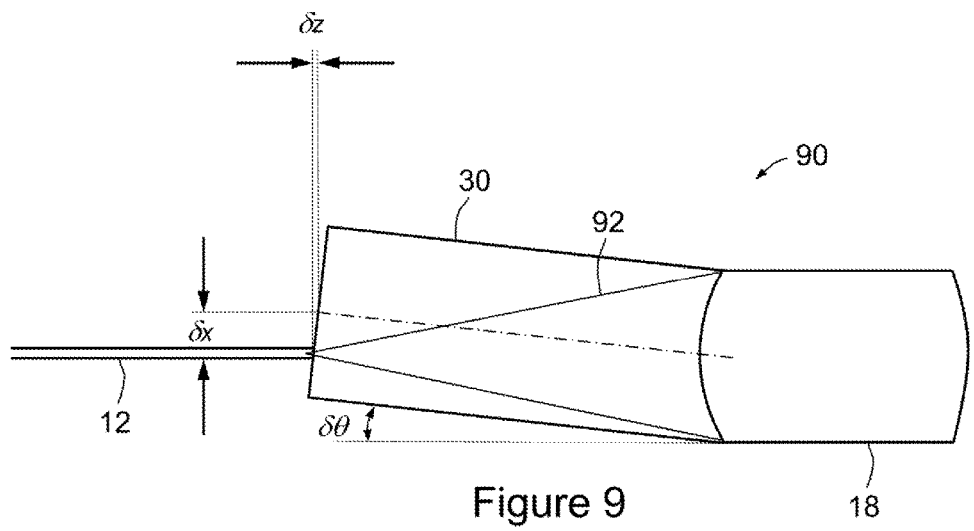
FIG. 9 is a schematic view of the compensation for lens alignment error according to an embodiment of the present invention.

These first of these properties is explained further by reference to FIG. 9, which is a schematic view of a lens group 90 (comparable to lens group 14 of FIGS. 2A to 3), but with misalignment between substrate 30 and aspheric lens 18. The effect of the misalignment can be almost entirely cancelled during active alignment by shifting the fibre attachment point sideways by an offset $\delta x$. With optical fibre 12 in its compensated position as shown in FIG. 9, the light cone emanating from optical fibre 12 propagates to aspheric lens 18 through almost exactly the same medium as it would in a perfectly aligned system. The only optical difference between the system of FIG. 9 and a perfectly aligned doublet is the small change $\delta z$ in the effective thickness of substrate 30 left after compensation; in the symbols of FIG. 3, this axial displacement is:

$$\delta z = (t_s + r_i)\frac{\sin^2\delta\theta}{\cos\delta\theta} \approx (t_s + r_i)\delta\theta^2 \quad \text{Equation 4}$$

For a long device with $t_s+r_i=10$ mm and a misalignment of even 1°, the above error is roughly 3 µm. Thus the error is transformed by active alignment into a small element thickness error, to which the designs according to this embodiment are largely insensitive. It is estimated that thickness errors must be of the order of 20 µm to seriously mar any of the performance of such devices. If the interface is a plane interface (radius=∞), any sideways misalignment between the elements of the lens group can be compensated for by a correcting sideways offset of the optical fibre.

Another manufacturing imperfection is the decentring of the spherical surface. Decentring may be described as a sideways offset between the spherical surface's centre and the distal aspheric surface's optical axis (viz, axis of rotational symmetry). This decentring causes the same kind of aberration, namely third order coma, as does a sideways offset from the optical axis of the fibre tip's position. Therefore, a deliberate sideways offset of the optical fibre tip can be used to cancel the third order aberration arising from the spherical surface's decentring. This cancellation, or "compensation" scheme, has been found to restore optical performance; that is, a system with the imperfections discussed above but compensated for by active alignment of the optical fibre tip position has almost the same optical performance (to within a few hundredths of a decibel) as an ideal system that is free of such imperfections.

It can therefore be seen that the effects of the main manufacturing imperfections can be cancelled by active alignment in the two element configuration of embodiments with two lens elements according to the present invention, such as that of FIGS. 2A and 2B.

Other potential sources of imperfection are lens element thickness errors, to which the embodiments of the present invention are substantially less sensitive.

Tolerance to Manufacturing Imperfections

Figure 10:
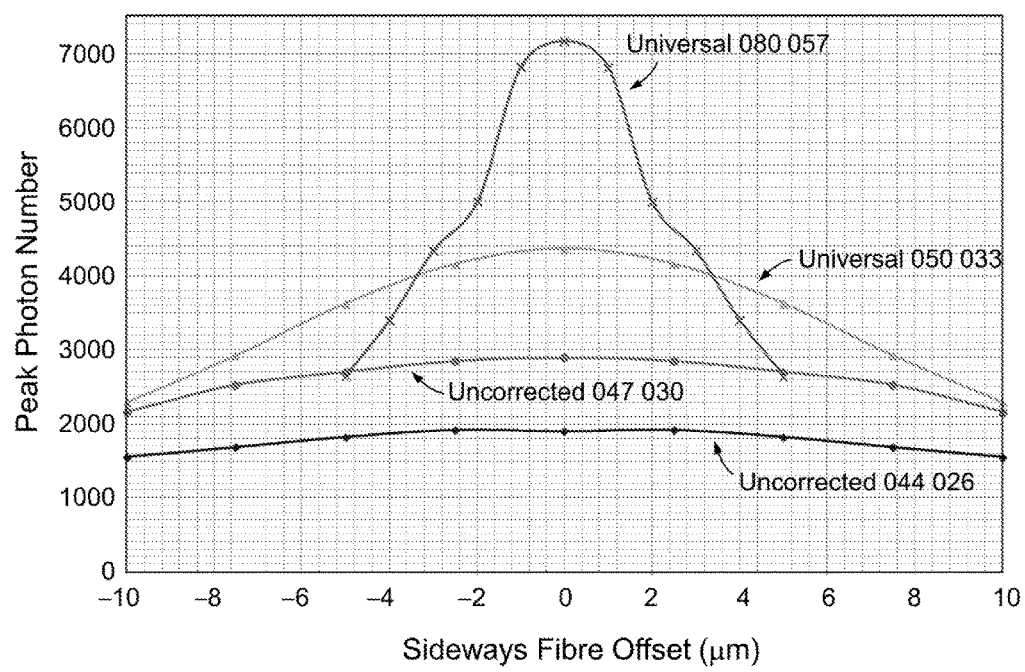
FIG. 10 is a plot of peak photon number returned for one-photon confocal microscopy as a function of drive fibre decentring for various embodiments of the present invention.

Electromagnetic field propagation through embodiments of the present invention that have two unlike glasses in the lens group with a spherical interface between them and an aspheric distal, adapted for use with excitation/fluorescence wavelengths in the broadened visible light spectrum of 450 nm to 850 nm has been simulated to determine likely performance and tolerance to foreseeable sources of manufacturing imperfection. FIG. 10 is a plot of the fluorescence light collected by a one-photon confocal microscope comprising optical system 10 (and variants thereof) as function of fibre offset (orthogonally to the optical axis) from its designed nominal, central position on the proximal face of substrate 30, expressed as Peak Photon Number v Fibre Offset (µm). The microscope has the characteristics given in Table 1, when imaging a subresolvable object containing 1000 sodium fluorescein fluorophores located at the focus of the system and the system is driven by 100 µW, 488 nm light source and has a pixel dwell time of 300 ns.

All of the calculations were done with a spherical wave electromagnetic field simulation method. (The system labelled "Universal 080 057" is described below.)

Figure 11:
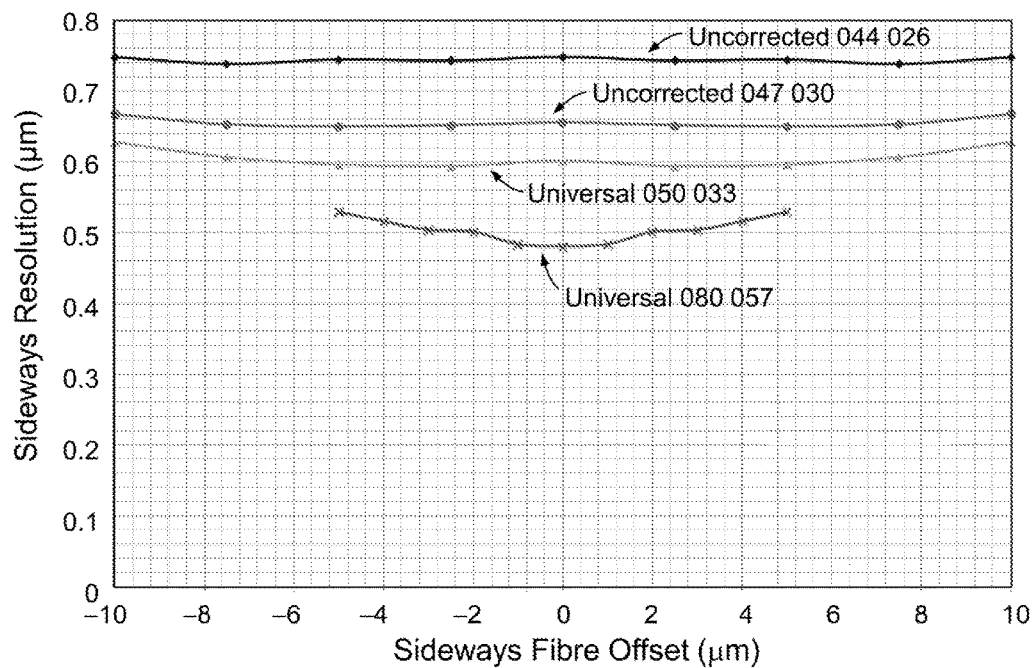
FIG. 11 is a schematic view of sideways resolution for one-photon microscopy as function of drive fibre decentring for various embodiments of the present invention.
Figure 12:
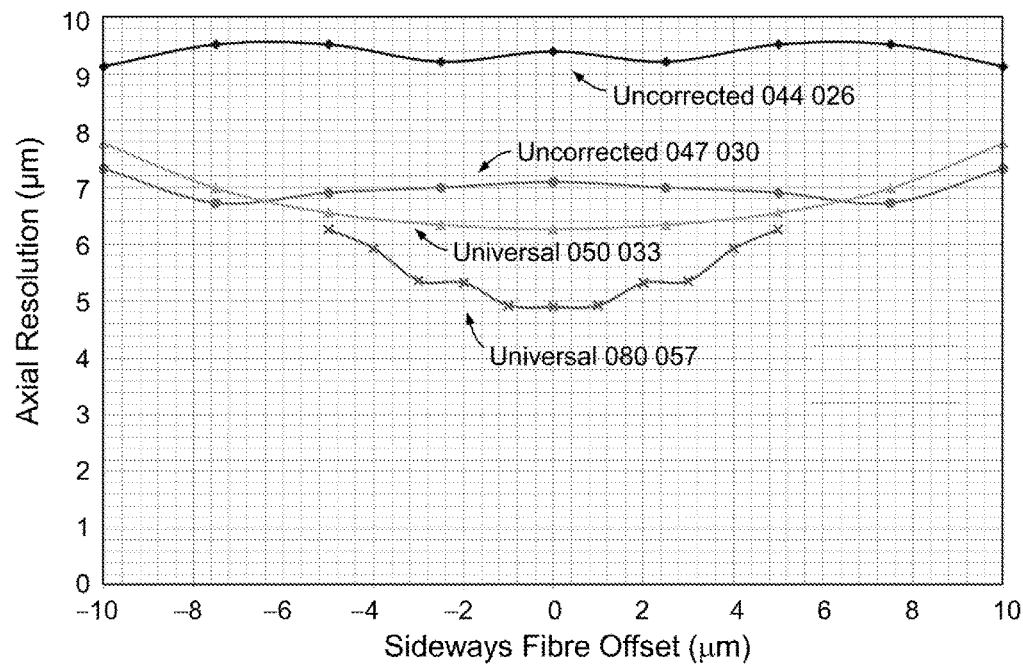
FIG. 12 is a schematic view of axial resolution for one-photon microscopy as a function of drive fibre decentring for various embodiments of the present invention.

FIGS. 11 and 12 are corresponding plots of lateral resolution and axial resolution, respectively.

These curves of falloff in performance, such as that of FIG. 10, show that active alignment method according to the present invention can be used to position the fibre accurately enough to compensate for such manufacturing imperfections, by studying the effects of both fibre and spherical interface misalignment together.

Figure 13:
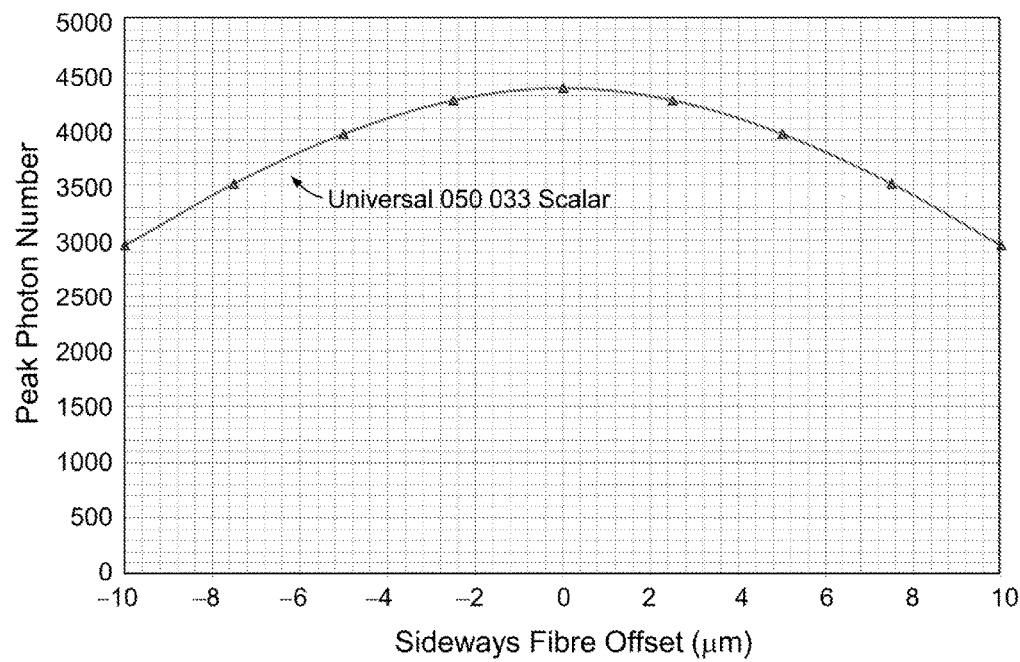
FIG. 13 is a plot of peak photon number returned for one-photon microscopy as function of spherical interface decentring for the "Universal 050/033" system of one embodiment of the present invention.
Figure 14:
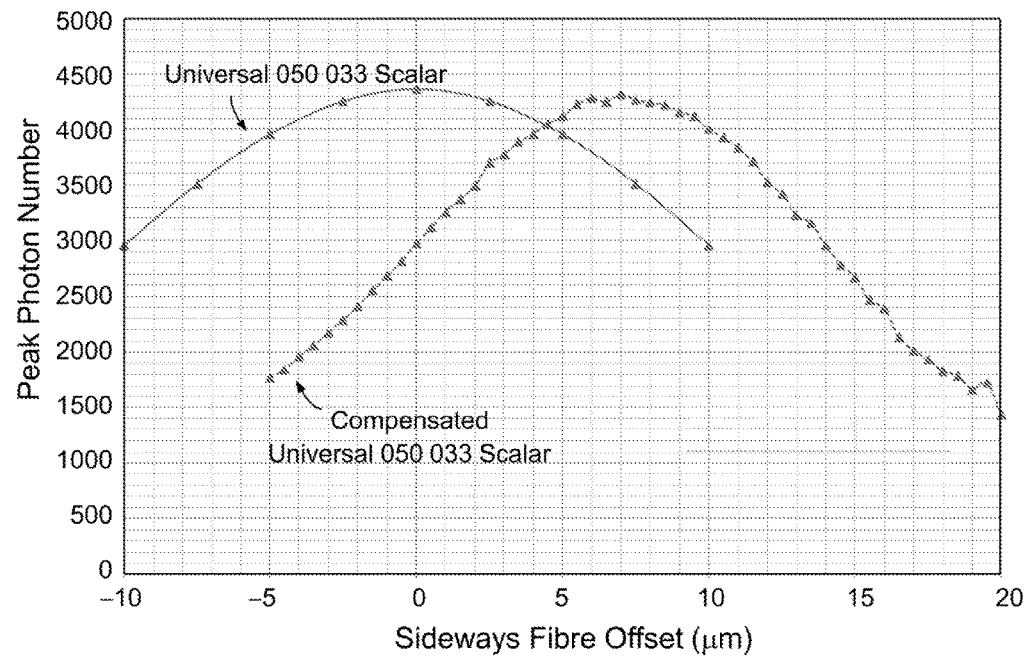
FIG. 14 is a plot of effectiveness of active compensation scheme peak photon number returned for one-photon microscopy as a function of fibre position for systems according to an embodiment of the present invention with a 10 μm spherical interface decentring.

FIG. 13 is a plot of falloff in performance, as measured by the number of photons collected by the chromatically corrected system as a function of the decentring of the spherical interface in microns. It will be seen that performance falloff is mild for decentrings of up to 5 µm, equivalent to an ISO10110-6 specification of roughly 4/40' (the interface radius is about 0.4 mm, so that 5 µm decentring is equivalent to a surface tilt of 5 µm/0.4 mm=0.0125 rad=40 minutes of arc). FIG. 14 reproduces the photon number curves of FIG. 10 (towards the left of that figure) together with the photon number as a function of fibre sideways position for "imperfect" systems marred by a spherical interface decentring of 10 µm. It will be seen from FIG. 14 that, for example, near perfect performance is restored by offsetting the fibre roughly 7.5 µm±2.0 µm when the system suffers a decentring of the spherical interface of 10 µm (equivalent to ISO10110-6 4/1° 20').

Figure 15:
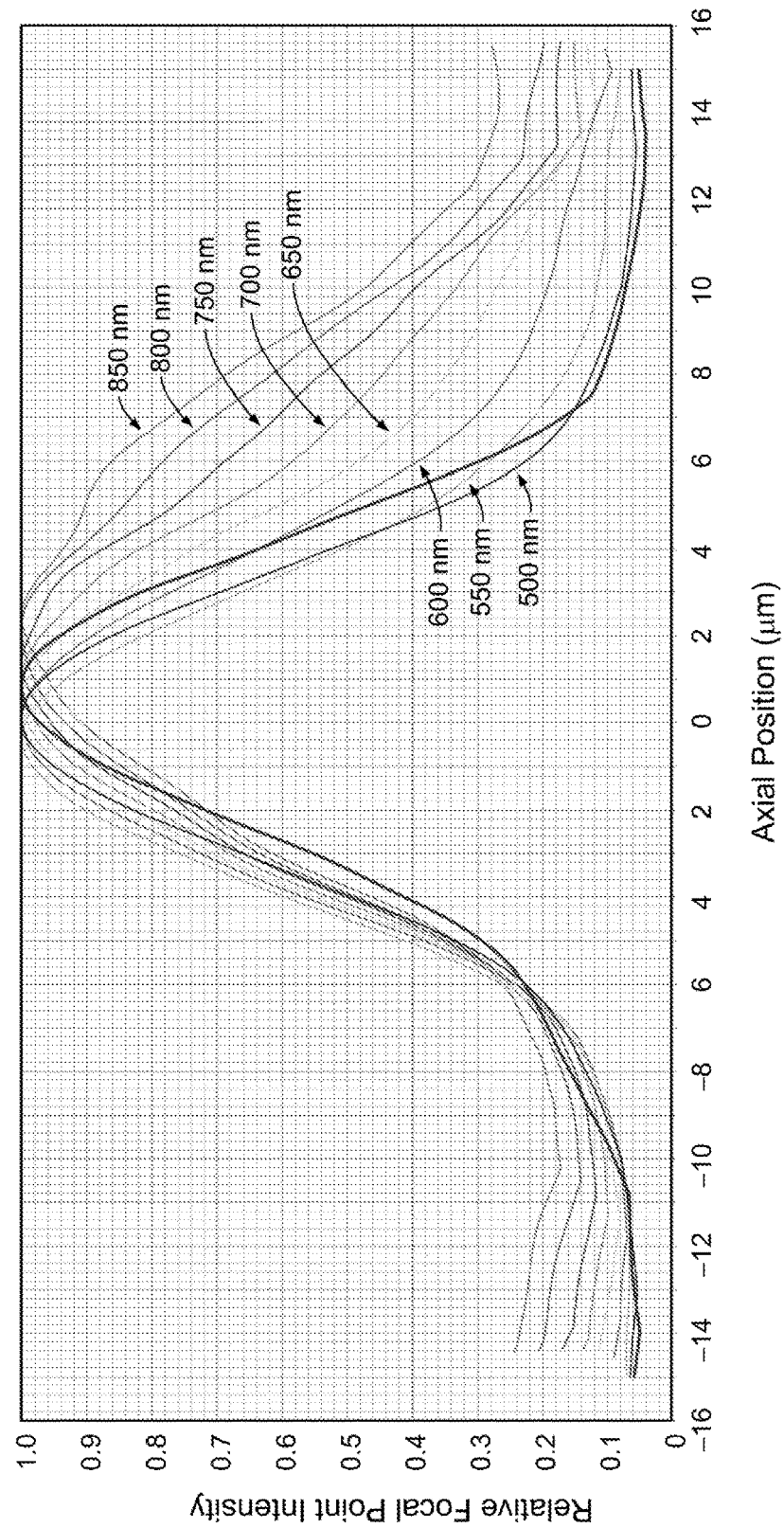
FIG. 15 is a plot of effectiveness of chromatic correction is a schematic view of axial responses for "Universal 050 033" system of one embodiment of the present invention for wavelengths in the wavelength range 450 nm to 850 nm.
Figure 16:
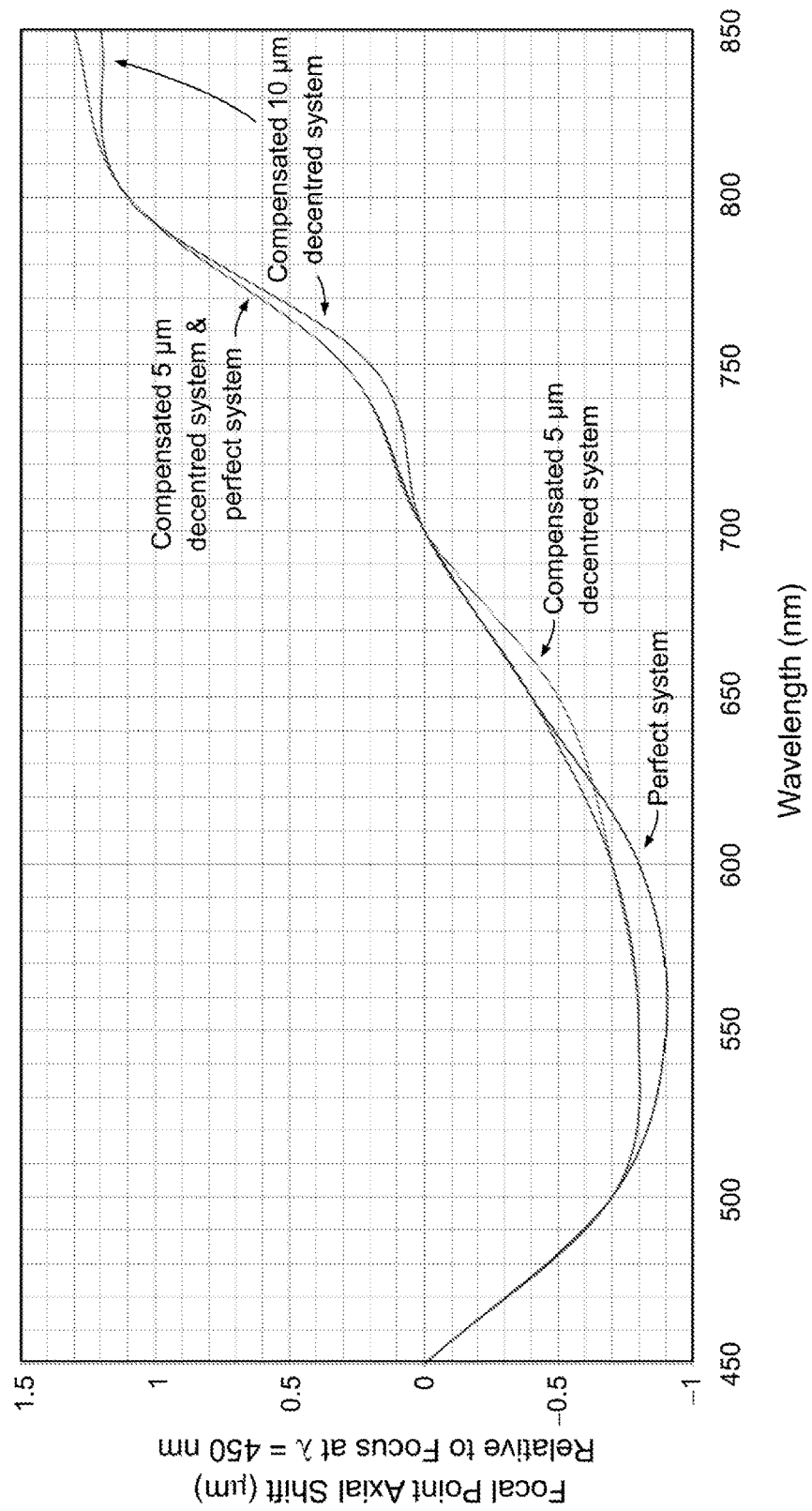
FIG. 16 is a plot of effectiveness of chromatic correction is a schematic view of Shift of axial focus position for the "Universal 050 033" system with wavelengths in the wavelength range 450 nm to 850 nm for ideal and compensated systems according to embodiments of the present invention.

As an indication of the effectiveness of chromatic correction according to this embodiment, the chromatic correction achieved by a "perfect" version of the system "Universal 050 033" is shown in FIG. 15 and summarised by FIG. 16. FIG. 16 shows the shift of the focal point for an ideal version of the system as well as versions that have spherical interface sideways offsets of 5 µm and 10 µm after these systems have been compensated by the appropriate fibre position shift.

When the system is marred by an imperfect positioning of the spherical interface (between substrate and aspheric lens), it has already been shown that near perfect optical performance can be restored by a compensating shift in the fibre position when one-photon imaging is being done with closely spaced fluorescence and driving wavelengths (e.g. 488 nm drive wavelength and 532 nm fluorescence peak). However, a system so compensated is no longer axissymmetric (i.e. no longer has rotational symmetry about the optical axis) owing to the oppositely offset fibre and spherical interface relative to the aspherical surface. Therefore, such a 'compensated' system also suffers lateral chromatic as well as axial chromatic shift.

Figure 17:
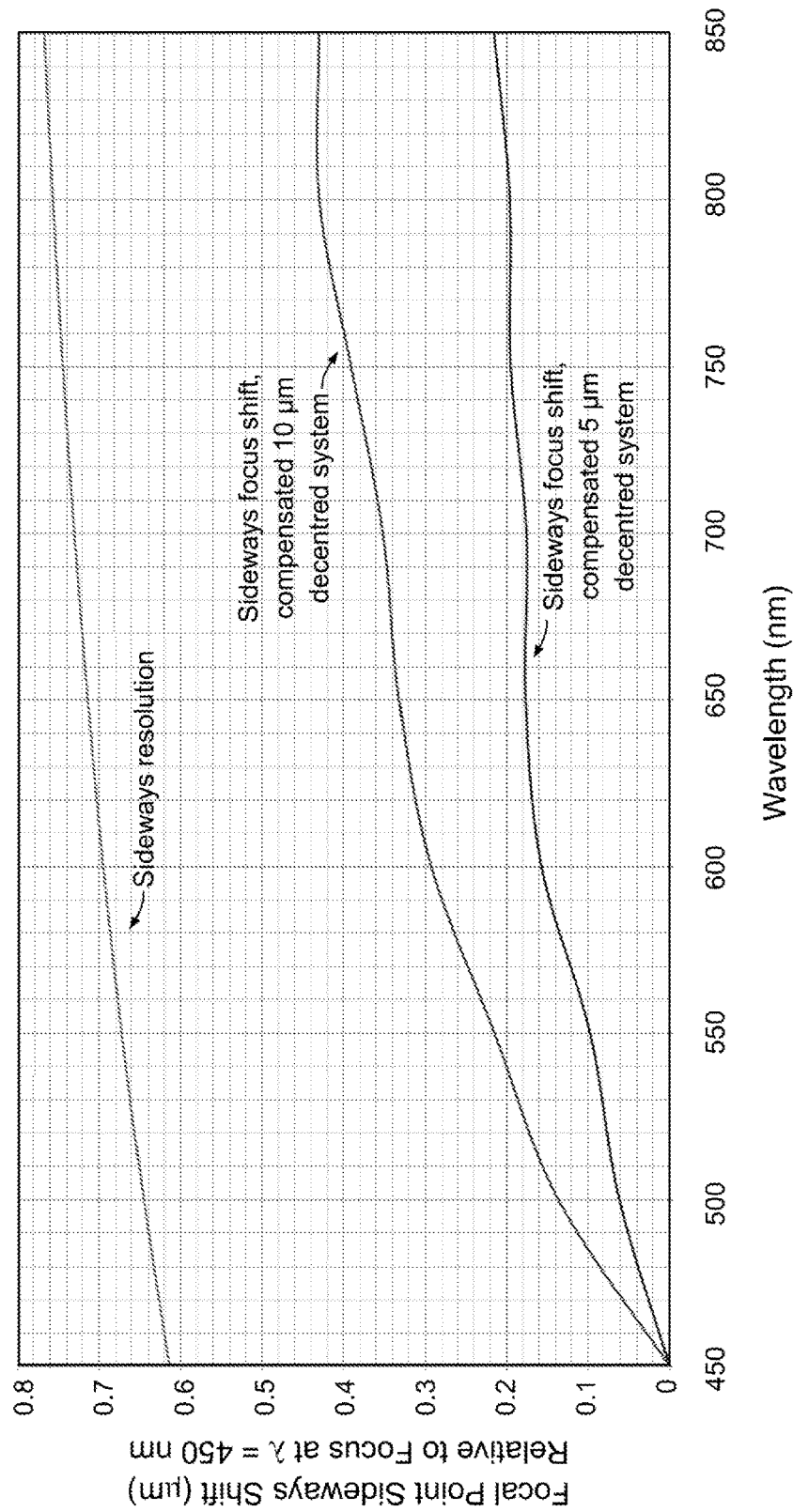
FIG. 17 is a plot of effectiveness of chromatic correction after compensation is a schematic view of sideways chromatic shift for the "Universal 050 033" system in the wavelength range 450 nm to 850 nm for ideal and compensated systems according to embodiments of the present invention.

FIG. 17 shows the sideways (lateral) shift of the fluorescence focus relative to the drive field focus in mm as a function of fluorescence wavelength for the "Universal 050 033" system when compensated by the appropriate fibre position offset for spherical interface decentrings of 5 µm and 10 µm, respectively (equivalent to ISO10110-6 4/40' and 4/1° 20', respectively). The ideal system, being axisymmetric, has no lateral chromatic shift. The same plot also shows the theoretical sideways confocal resolution:

$$\Delta x = \frac{2}{\pi NA} \frac{\lambda_d \lambda_f}{\sqrt{\lambda_d^2 + \lambda_f^2}} \quad \text{Equation 5}$$

where $\lambda_d$ is the driving or excitation wavelength and $\lambda_f$ the fluorescence peak wavelength. Equation 5 is the confocal system analogue of the Airy disk lateral resolution formula for a brightfield, unapodised system (here $\omega_{1,1} \approx 3.83$ is the first zero of the first kind Bessel function of order 1):

$$\Delta x = \frac{\omega_{1,1}\lambda}{2\pi NA} \approx 0.61 \frac{\lambda}{NA} \quad \text{Equation 6}$$

The full width half maximum resolution is $\sqrt{\log_e 2} \approx 0.833$ times the value given by Equation 5.

Figure 18:
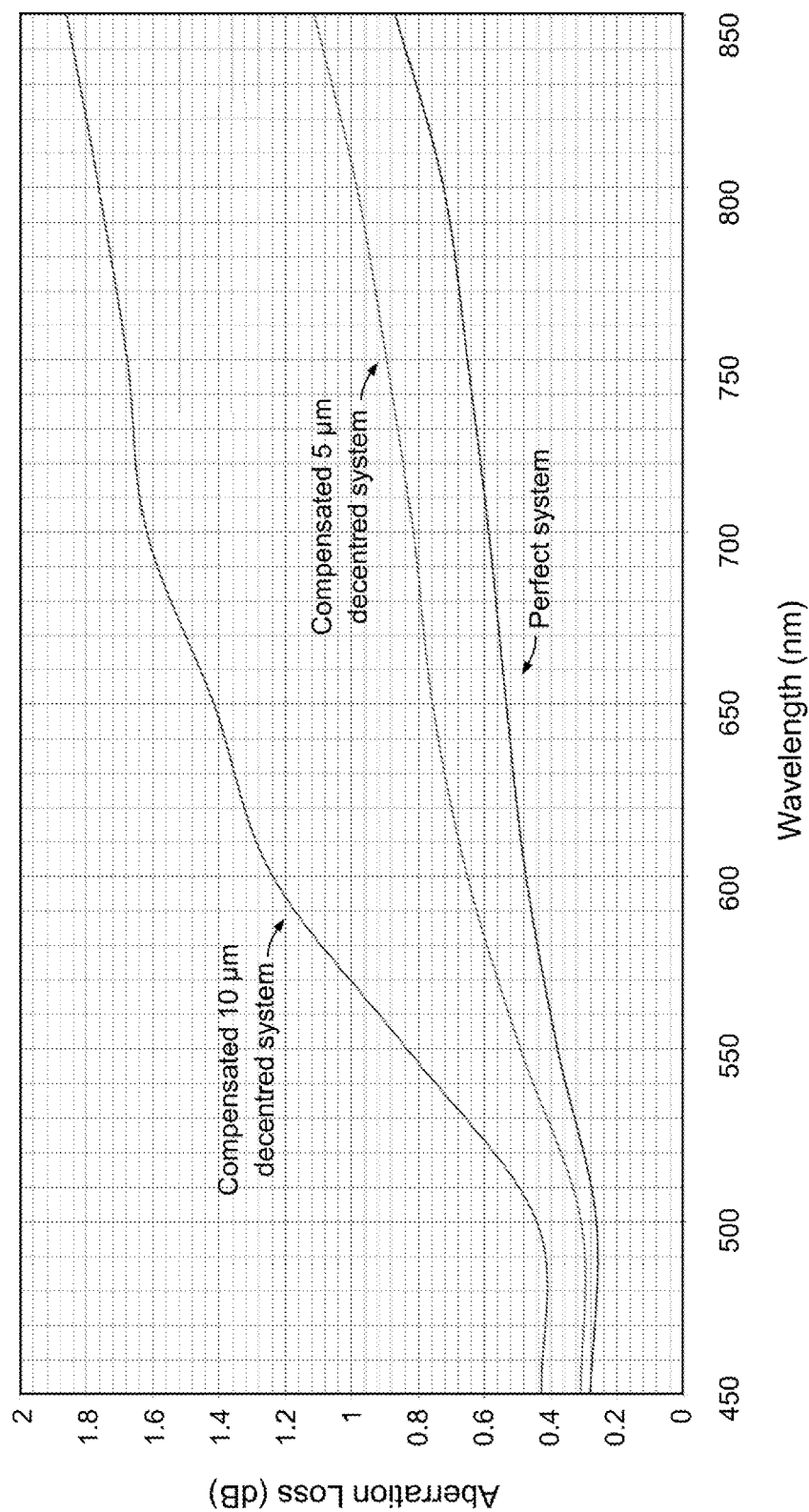
FIG. 18 is a plot of effectiveness of chromatic correction after compensation is a schematic view of aberration loss for the "Universal 050 033" system in the wavelength range 450 nm to 850 nm for ideal and compensated systems according to embodiments of the present invention.
Figure 19:
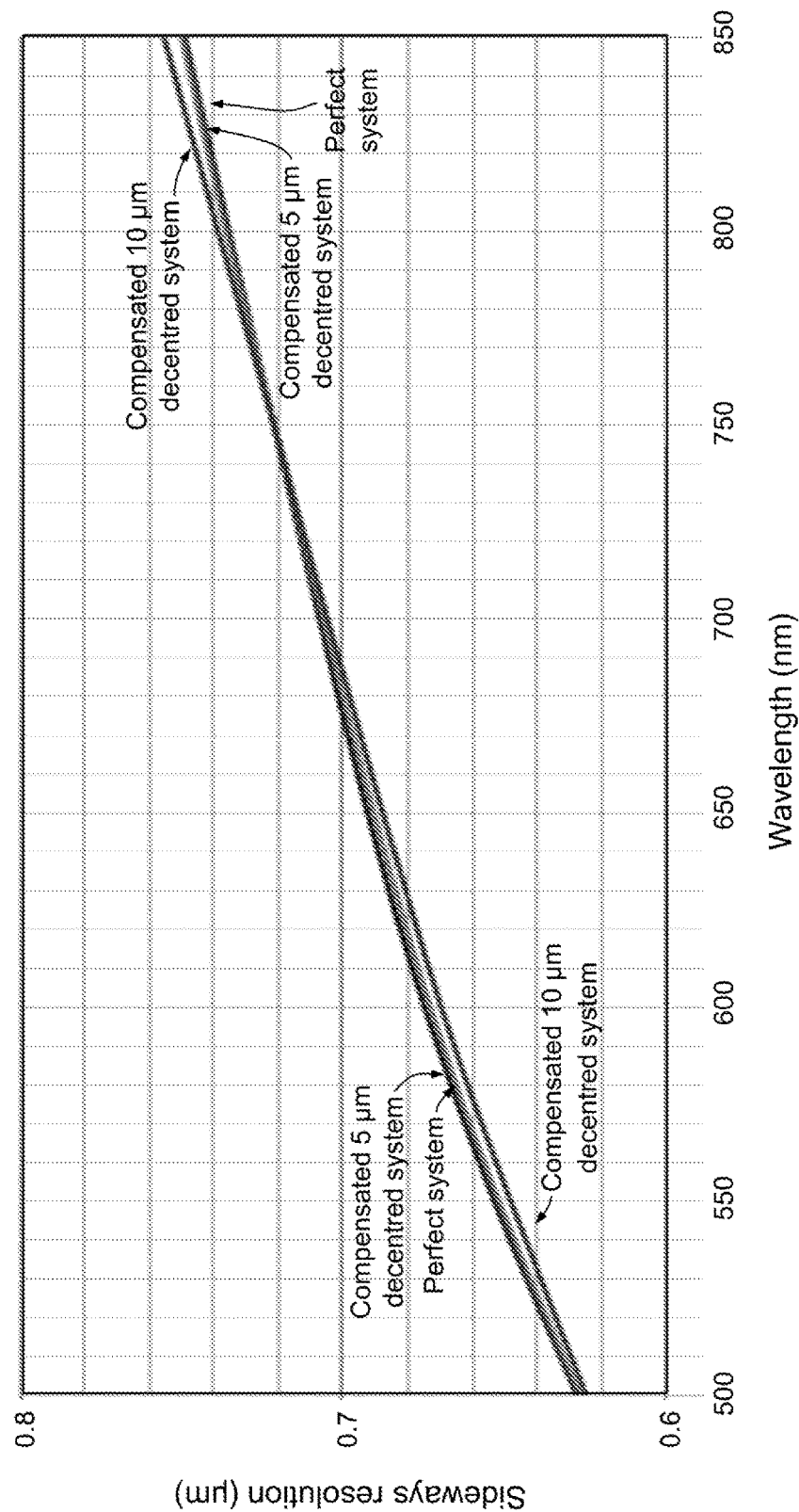
FIG. 19 is a plot of effectiveness of chromatic correction after compensation is a schematic view of sideways resolution for the "Universal 050 033" system in the wavelength range 450 nm to 850 nm for ideal and compensated systems according to embodiments of the present invention.

FIG. 18 is a plot of the aberration loss for the "Universal 050 033" system in the wavelength range 450 nm to 850 nm for ideal (i.e. with no decentring, offsets or other manufacturing imperfections) and compensated systems, and is indicative of the effectiveness of chromatic correction after compensation. FIG. 17 shows that the sideways chromatic shifts for the compensated systems with 5 µm and 10 µm decentring of the spherical interface are well less than the confocal resolution, so that the aberration loss (as plotted in FIG. 18) due to the imperfection is only 0.22 dB more than in the "perfect" case for the 5 µm decentred system and less than 1 dB more for the 10 µm system. Likewise, the plots of lateral resolution as functions of wavelength for the decentred systems are almost the same as the theoretical value; this is shown in FIG. 19, which is a plot of the sideways resolution of the "Universal 050 033" system in the wavelength range 450 nm to 850 nm for ideal and compensated systems.

It can thus be seen that such systems, with two unlike glasses in the lens group, a spherical interface therebetween and an aspheric distal surface, can be used to perform one photon confocal imaging with any number of pairs of driving and fluorescence wavelengths within the extended band 450 nm to 850 nm, yet still bring all imaged wavelengths to essentially the same focus. This allows true multichannel one photon confocal imaging for any number of pairs within that wavelength band.

Figure 20:
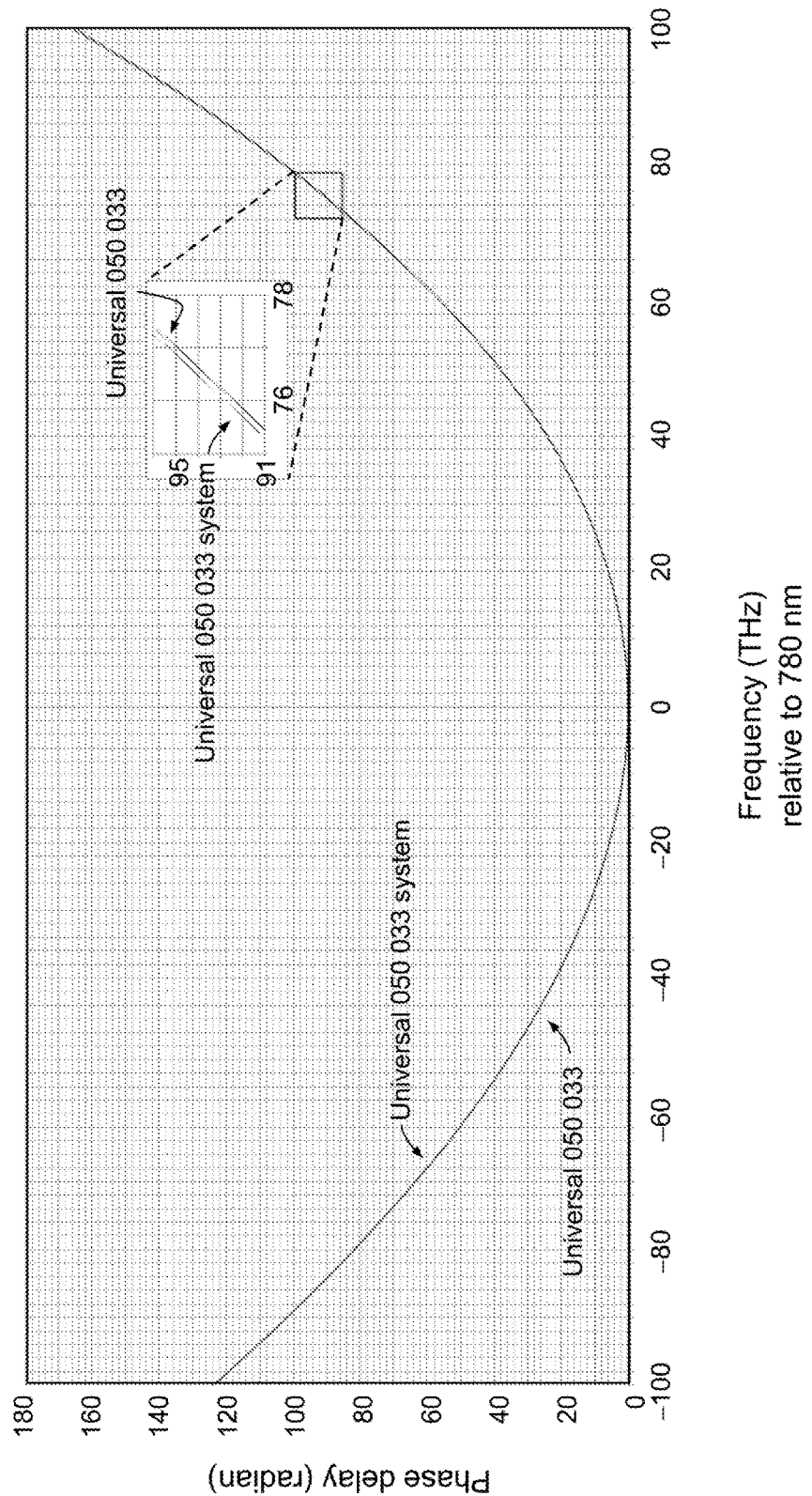
FIG. 20 is a plot of phase response for whole systems and for central ray alone for the "Universal 050 033" system according to an embodiment of the present invention.
Figure 21:
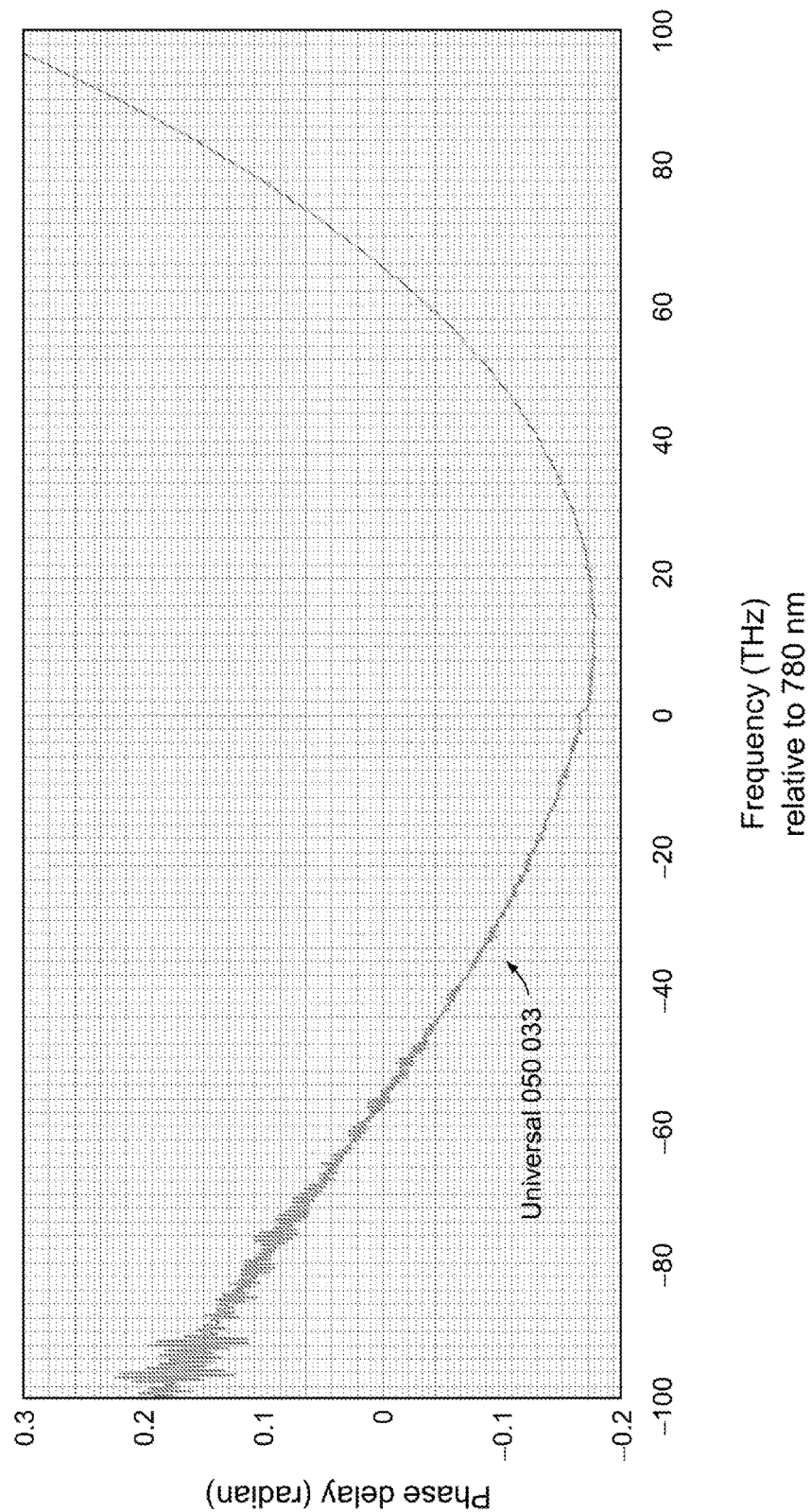
FIG. 21 is a plot of multipathing phase (phase relative to central ray) for the "Universal 050 033" system according to an embodiment of the present invention.

These systems may also be used for two and multi-photon imaging, with different levels of efficacy. The success of such imaging systems depends on the delivery of very narrow pulses, down to 100 fs or less in width. Lens systems, if uncorrected, can compromise pulsewidth. Lens systems introduce pulse spreading in two components: the first is the unavoidable material dispersion, whose dependence on frequency is smooth and well approximated by a quartic dependence on frequency. Its dependence is thus very much like the dispersion introduced by delivery fibres and can thus almost perfectly be compensated for by e.g. compensating gratings or dispersion compensating fibre. The second component is the "multipathing" component; it may be regarded as arising from the difference between the time of flight for noncentral rays and the chief ray propagating along the optical axis through the lens system. Bad multipathing leads to swift phase variation with frequency and cannot be compensated for by gratings or dispersion compensating fibres. For an uncorrected lens, a simple estimate of the time of flight difference between the marginal and chief ray is given by:

$$|\Delta\tau| \approx \frac{NA^2 F\lambda}{2c(\lambda_F - \lambda_C)V_d} \qquad \text{Equation 7}$$

where F is the focal length, $\lambda$ the central working wavelength, c the freespace lightspeed, $\lambda_F$ and $\lambda_C$ the Fraunhoffer F- and C-line wavelengths and $V_C$ the Abbe number calculated from these lines. For systems in this document, with NA≈0.4, this uncorrected formula yields an estimate of 122 fs. However, if the actual, corrected phase response of these three systems is calculated for a 200 THz wide band centred at 384.3 THz (corresponding to wavelengths between 619 nm and 1054 nm and a centre wavelength of 780 nm), the outcome is as shown in FIG. 20, where the phase responses for the whole system and the phase of the central ray alone for each system are shown for the three systems. They are seen to be almost the same in each case; the difference phase, i.e. the second "multipathing" phase delay spoken of above, is shown in FIG. 21. The fine structure in FIG. 21 is due to the interference between light components that run along the many different possible paths through the lens group and the slightly imperfect equalising of all these paths by the chromatic correction.

Figure 22:
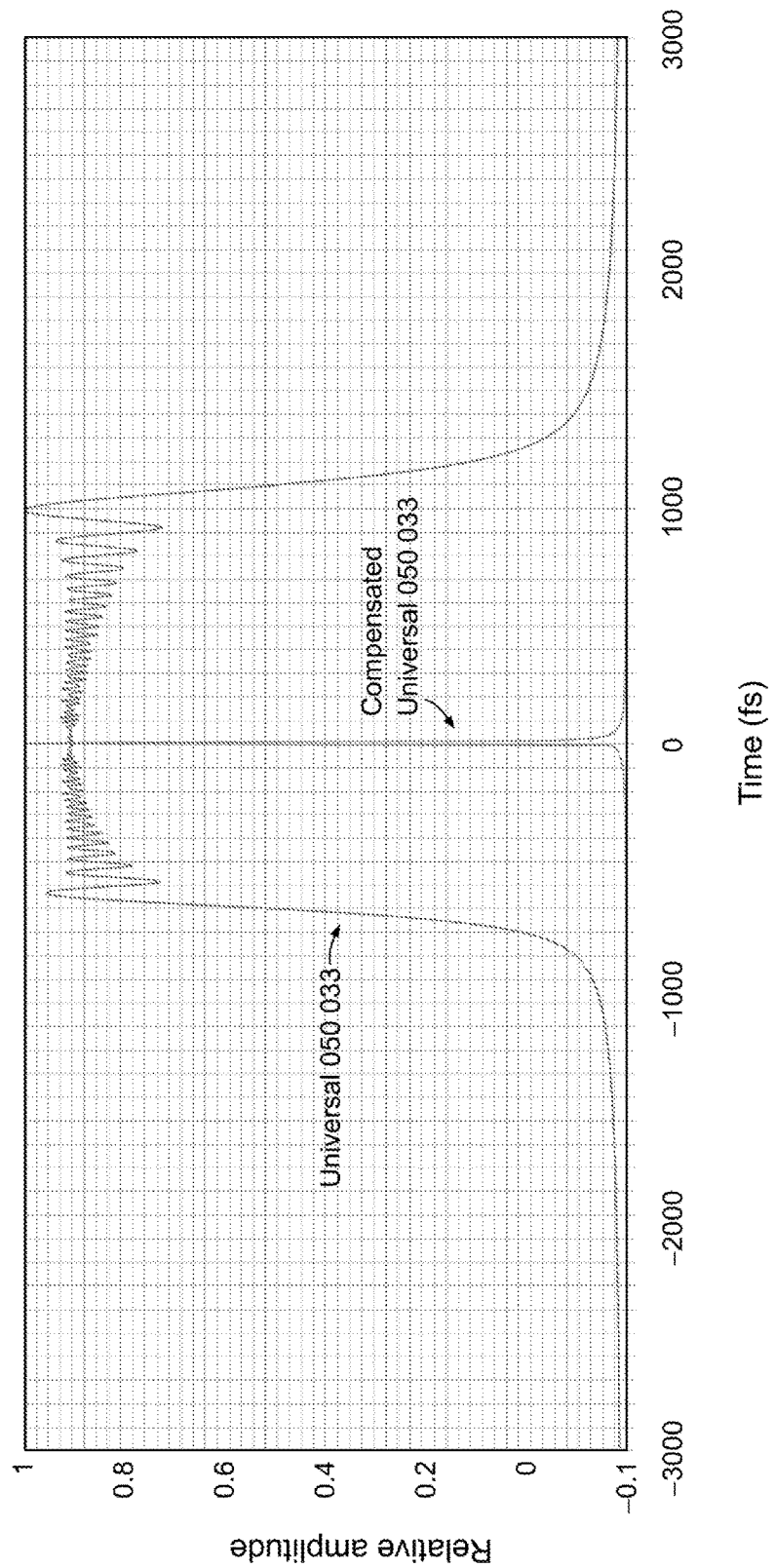
FIG. 22 is a schematic view of output pulses from uncompensated and compensated systems according to embodiments of the present invention.
Figure 23:
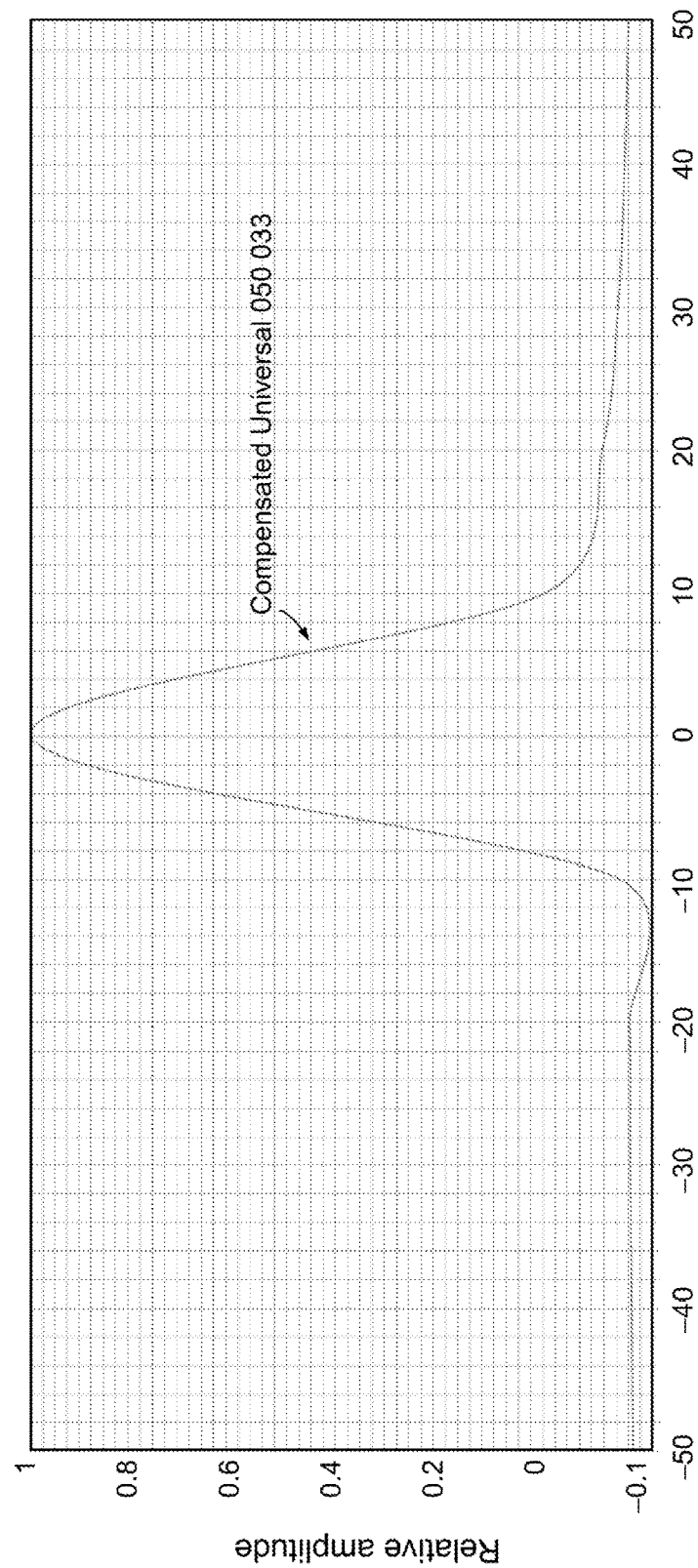
FIG. 23 is a schematic view of output pulses from compensated systems according to embodiments of the present invention.

The corresponding time domain output responses when a 10 fs wide light pulse with time dependence (here $\tau$=10 fs and $\lambda_c$=780 nm):

$$f(t) = \text{sinc}\left(\frac{2\pi t}{T}\right) e^{-i\frac{2\pi ct}{\lambda_c}} m \qquad \text{Equation 8}$$

is input into the system are shown in FIGS. 22 and 23; FIG. 22 shows the response from the whole lens system before the material dispersion has been compensated for with the compensated pulses overlain to show the relative size, whereas FIG. 23 shows the pulse broadening owing to multipathing alone. It is clear that the chromatic correction for each system keeps the multipathing delay to less than 20 fs, much less than the 122 fs uncorrected value above.

Current group delay compensation with chirped gratings can realise a pulse of about 50 fs width; FIG. 23 makes it clear that these systems are more than well enough corrected not to hinder this degree of compensation and will only begin to show themselves as significant contributors to pulse broadening when 20 fs pulses or less can be realised by compensated systems.

Two photon imaging often requires very high powers for good signal to noise. Calculations for fluorescein show that powers of 10 mW to 5 W depending on the application are wonted. However, the very high clarity (low absorptivity) of optical glasses means that the direct bonding of the lens group to the scanning fibre without an intermediate air gap will not damage the lens from thermal loading at these high powers. Schott indicate a transmittance of roughly 0.995 through 25 mm of N-SF66 glass, corresponding to an absorption co-efficient of 0.2 m$^{-1}$.

Figure 24:
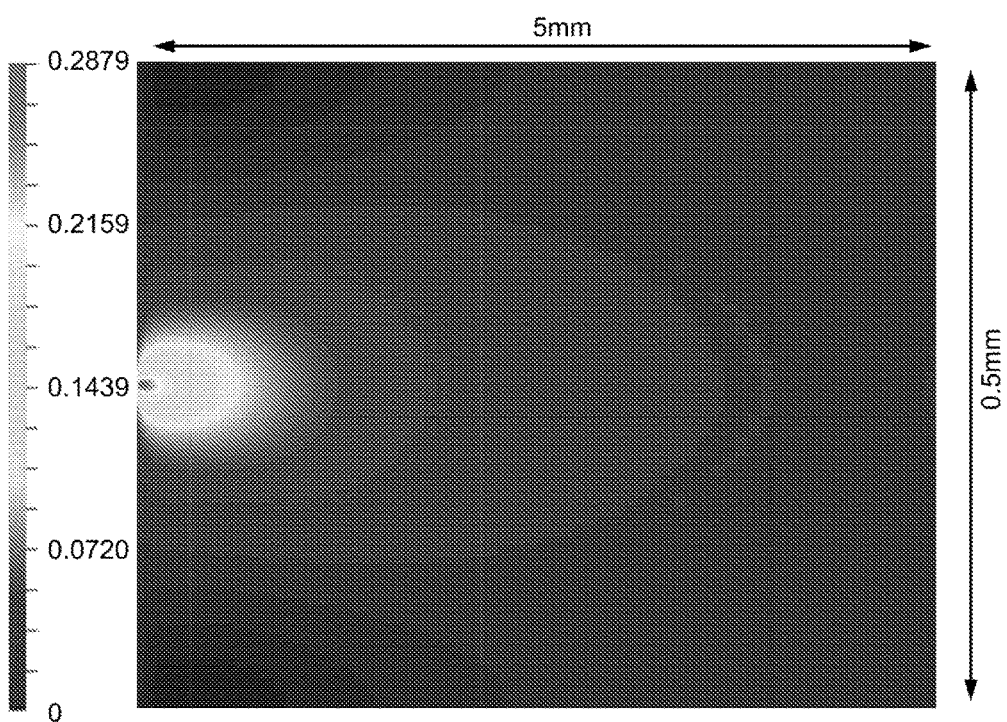
FIG. 24 is an image of local heating by 1 W 0.1 NA beam diffracting through a Schott N-SF66 glass rod of dimensions ø 0.5 mm×5 mm.

With this absorption co-efficient, FIG. 24 shows the steady-state temperature rise, relative to the outside of the rod, in a Schott N-SF66 rod of 0.5 mm diameter and 5 μm length when a 1 watt beam of 0.1 NA is input to the left hand side of the rod. These conditions correspond to the light input to the "Universal 050 033" system discussed above. Here it is assumed that the rod is cooled highly effectively by convection owing to its being swiftly scanned in air, so that the rod's edge is held near to the ambient temperature. Less than 100 μW is absorbed by the rod itself, and the temperature rise is less than one Kelvin. (The peak rise in FIG. 24 is 0.288 K.)

The systems discussed above have a simplicity making for easy construction. However, practical refractive embodiments seem limited to numerical apertures of about 0.5, and achieve these only with significant vignetting losses.

According to a second group of embodiments of the present invention, there are provided optical systems comprising a first lens group of two or more unlike glasses and, in addition, a second lens group of one or more elements located forward of the first lens group; in some of these embodiments there is a gap between the first and second lens groups (which may be, for example, an air-gap or freespace). This combination of lens groups provides mutually cancelling dispersion, and is adapted for a driving/fluorescence wavelength pair (including cases where fluorescence and driving wavelengths are the same) in the broadened light spectrum of 450 nm to 850 nm wavelength. This permits higher numerical apertures, though at the expense of greater complexity and greater manufacturing difficulty.

The most practical of such embodiments includes such an airgap or freespace. An optical system according to such an embodiment is shown schematically at 100 in FIG. 25. Optical system 100 includes (from proximal end to distal end) a first lens group 102 comprising a collimator doublet 104a, 104b that collimates light emerging from a delivery optical fibre (not shown). Collimator doublet 104a, 104b is followed by a gap 106 of freespace, and then a second lens group 108. Second lens group 108 comprises a beam-shrinking or collimating element 110a of a low index, low dispersion glass (such as Schott N-FK51A) and an aspheric lens 110b of a higher index higher dispersion glass (such as Schott N-LAK34). Beam-shrinking or collimating element 110a slightly shrinks the collimated beam, working as a low magnification Galilean telescope. Aspheric lens 110b converts the resulting beam to the output focus. Beam-shrinking or collimating element 110a adds positive or negative power to the beam depending on wavelength to cancel the dispersion effects of collimator doublet 104a, 104b and aspheric lens 110b. Second collimator doublet element 104b and second lens group 108 are located in a cylindrical housing sleeve 112. A coverslip is shown at 114.

Figure 25:
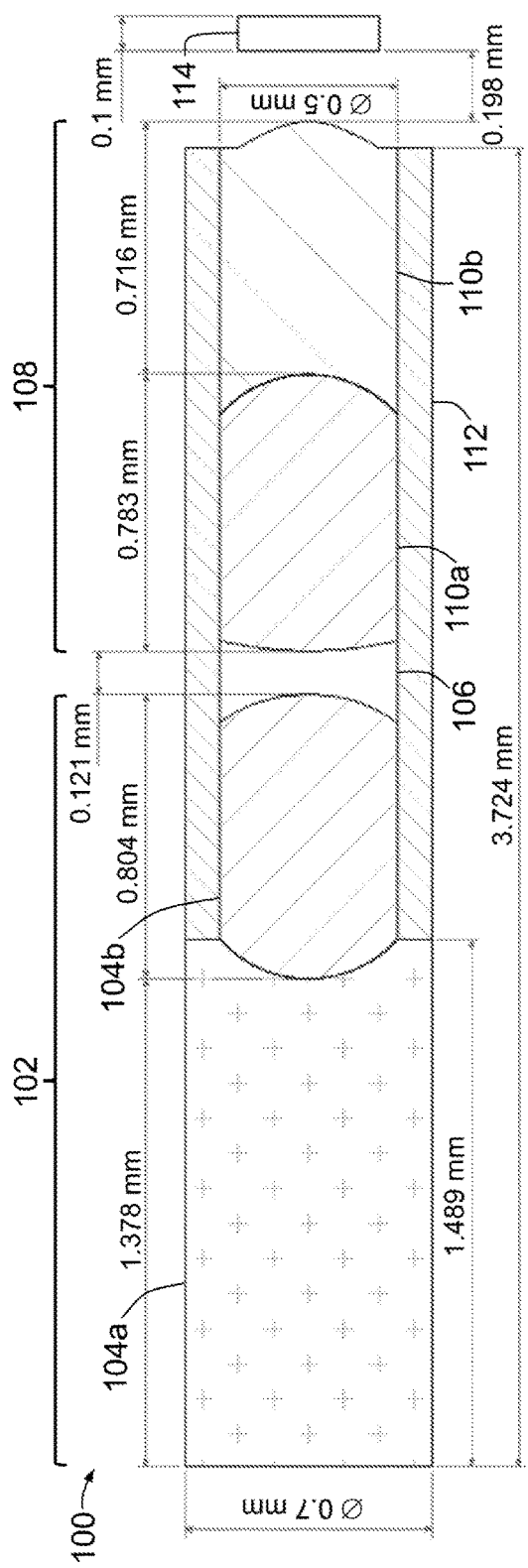
FIG. 25 is a schematic view of a "Universal 0.80/0.57 NA" system according to an embodiment of the present invention at 70:1 scale.
Figure 26:
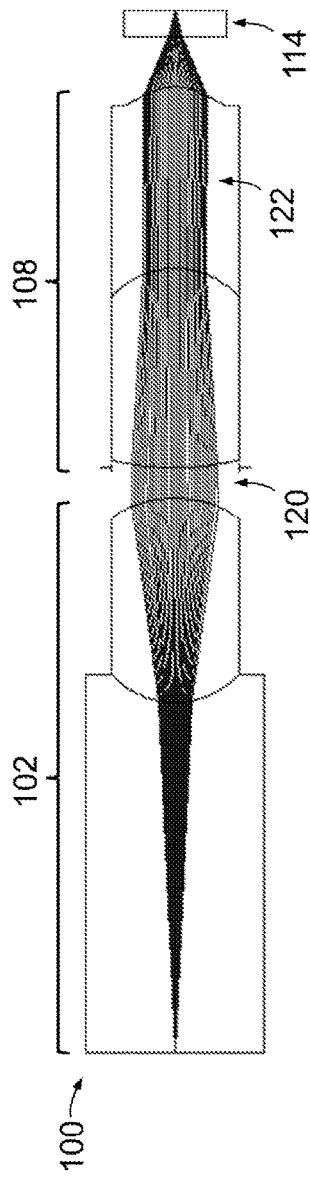
FIG. 26 is a schematic view of twofold collimation in the system of FIG. 25.

The optical performance of optical system 100 of FIG. 25 was simulated, as is shown in ray-tracing plot 120 of FIG. 26 (in which collimated beam portions 120 and 122—in freespace gap 106 and aspheric lens 110b respectively—are indicated). The properties used for optical system 100 in that simulation, in particular the surface, centre thickness and material data, are presented in Table 3, its optical performance is presented in Table 4 and its mechanical performance in Table 5.

TABLE 3

Characteristics of Lens Groups of FIGS. 25 and 26

| Surface no. | Radius (mm) | Quadratic aspheric coefficient ($mm^{-1}$) | Quartic aspheric coefficient ($mm^{-3}$) | Sextic aspheric coefficient ($mm^{-5}$) | Surface centre thickness (mm) | Material | D (mm) | Description |
|---|---|---|---|---|---|---|---|---|
| 1 | ∞ | 0.000000 | 0.000000 | 0.000000 | 1.378065 | N-SF66 | 0.7 | Planar; fibre bonded to its centre |
| 2 | 0.337850 | 0.000000 | 0.000000 | 0.000000 | 0.804024 | N-FK51A | 0.5 | Fibre collimator inside surface |
| 3 | −3.588523 | −0.857541 | −5.923243 | 23.075341 | 0.120865 | Freespace | 0.5 | Fibre collimator output aspheric surface |
| 4 | ∞ | 0.000000 | 0.000000 | 0.000000 | 0.000000 | Freespace | 0.5 | Aperture stop |
| 5 | 1.069905 | 0.000000 | 0.000000 | 0.000000 | 0.782923 | N-FK51A | 0.5 | Galilean telescope input (collimated beam) |
| 6 | −0.333333 | 0.000000 | 0.000000 | 0.000000 | 0.716058 | N-LAK34 | 0.5 | Galilean telescope output (collimated beam) |
| 7 | −0.833702 | −2.181091 | 34.697849 | −335.167203 | 0.198088 | Freespace | 0.4 | Final Focussing Surface |
| 8 | ∞ | 0.000000 | 0.000000 | 0.000000 | 0.100000 | N-BK7 | 0.4 | Coverslip Input |
| 9 | ∞ | 0.000000 | 0.000000 | 0.000000 | 0.000000 | Watery tissue | 0.4 | Exemplary specimen tissue |

The collimation between first and second lens groups 102, 108 is not quite perfect, so that adjustment of the relative positions of the two lens groups 102, 108 introduces spherical aberration to the beam. Thus, spherical aberration arising from imperfect axial siting of the refracting surfaces can be corrected by a compensating adjustment to the separation between the two lens groups 102, 108. Comatic aberration arising from imperfections can be compensated for by an adjustment of the input optical fibre's lateral position. Owing to the many surfaces in system optical 100, however, there may also be astigmatic aberration in this optical system; if necessary, an active compensation method can be used to adjust the lateral position of second lens group 108 relative to first lens group 102. Such methods employ:
  i) An oversize bore in the housing sleeve 112 or an undersize outer diameter of second lens group 108; and
  ii) Access ports through housing sleeve 112 to admit push rods for adjusting the relative position and also to daub second lens group 108 with glue to cement its optimal position after active alignment.

TABLE 4

Optical Performance of optical system 100 of FIGS. 25 and 26

| System Parameter Name | Symbol | Value |
|---|---|---|
| System Drive Wavelength | $\lambda_D$ (nm) | >450 |
| System Fluorescent Wavelength | $\lambda_F$ (nm) | <850 |
| System Output Numerical Aperture (Petermann II) | $\eta_{out}$ | 0.57 (0.80) |
| Petermann II System Lateral Resolution | $\Delta x_{FWHM}$ (μm) | 0.48 |

TABLE 4-continued

Optical Performance of optical system 100 of FIGS. 25 and 26

| System Parameter Name | Symbol | Value |
|---|---|---|
| System Axial Resolution (FWHM) | $\Delta z_{FWHM}$ (μm) | 4.9 |
| Strehl Ratio at $\lambda_D$ | $S_D$ | 0.91 (0.82) |
| Strehl Ratio at $\lambda_F$ | $S_F$ | 0.92 (0.88) |
| Total Loss (one pass)[1] | $L_V$ (dB) | 1.4 |
| Photon Number (fluorescence confocal microscopy)[2] | N | 7170 |

[1] At 488 nm wavelength; the full, there-and-back loss in fluorescence one photon microscopy, e.g. with FITC, is roughly twice this value

[2] Total number of returned photons gathered by one-photon fluorescence microscopy imaging of subresolvable fluorophore containing 105 fluorescein ions with 100 μW of 488 nm driving light in the 0.095 NA SM450 optical fibre and 300 ns dwell (i.e. photon gathering) time

TABLE 5

Mechanical Performance Parameters for Optical System 100 at 1 mm Amplitude Scan

| Mechanical Performance Parameter Name | Symbol in FIGS. 2 & 3 | Universal 0.80/0.57 NA | Datum |
|---|---|---|---|
| Ellipsoidal window inside principal curvature radii | $r_1, r_2$ (mm) | 2.71, 10.5 | N/A |
| Bearing to magnet fibre span | $l_C$ (mm) | 4.0 | N/A |
| Fast scan resonant frequency | $f_{res}$ (kHz) | 0.7939 | 0.8734 |
| Driving force amplitude for fast scan direction | $F_{fast}$ (µm) | 452 | 161 |
| Sideways magnet displacement amplitude for fast scan direction | $\delta_{fast}$ (µm) | 170 | 97 |
| Driving force amplitude for slow scan direction | $F_{slow}$ (mN) | 6.10 | 5.85 |
| Sideways magnet displacement amplitude for slow scan direction | $\delta_{slow}$ (µm) | 465 | 200 |

Optical systems according to a third group of embodiments of the present invention employ an optical fibre that has a highly multimoded secondary core that can accept and guide return fluorescence. This simplifies the design of the fluorescence return path and thus yields a simplified system fit for many-photon imaging, with modest aberration correction.

Figure 27:
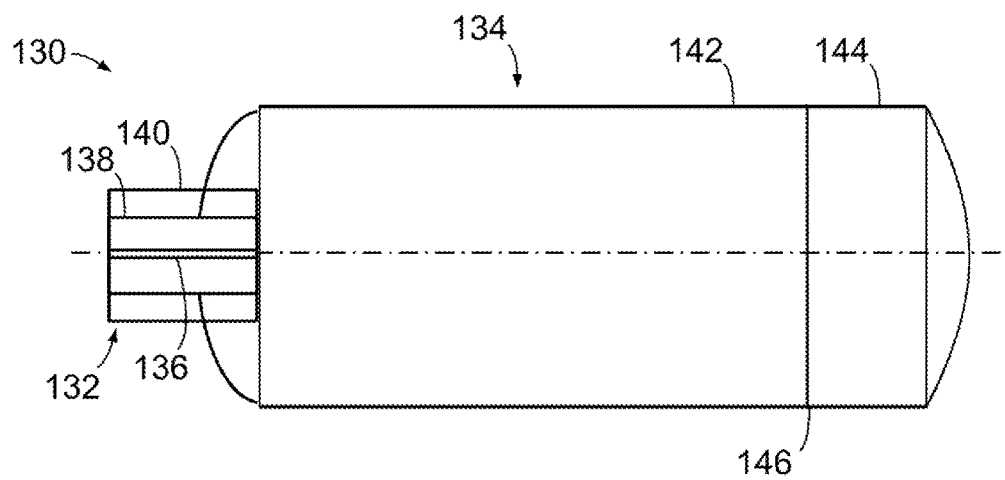
FIG. 27 is a schematic view of non descanned many-photon system according to an embodiment of the present invention.

FIG. 27 is a schematic view of a non-descanned many-photon optical system 130 comprising an optical fibre 132 and a lens group 134, according to this third group of embodiments. Optical fibre 132 comprises a central one moded driving core 136 that powers the system at the many-photon driving wavelength, surrounded by a multi-moded fluorescence gathering core 138 that collects many-photon fluoresced return light, and is itself surrounded by fibre cladding 140. Lens group 134 comprises a substrate 142, an aspheric lens 144 and a planar interface 146 therebetween. Lens group 134 sets up an intense focus in the specimen (such as biological tissue). Many-photon fluoresced light is imaged back into mulimoded fluorescence gathering core 138, whose high multimodedness fluorescence means that it accepts and guides fluorescence even though its wavefront may be considerably aberrated. Thus the need to chromatically correct the lens group is avoided, and a scanning microscope or endoscope that includes optical system 130 can work as a non-descanned many-photon system.

Optical systems according to a fourth group of embodiments of the present invention employ one or more auxiliary lightguiding cores located in the scanning optical fibre (which may be referred to as 'navigator' cores), so that the imaging numerical aperture can be switched between the main, high resolution value (using the centreral imaging core) to a low value (say, 0.1 NA) using the one or more navigator cores. If there are a plurality of such navigator cores, it is possible to provide one or more intermediate steps of successfully higher resolution. This approach allows a user to position an image easily, with coarse axial resolution and high tolerance to siting errors and hand unsteadiness, and then switch to a high resolution mode (with lower tolerance) once the target tissue has been identified or located.

Figure 28:
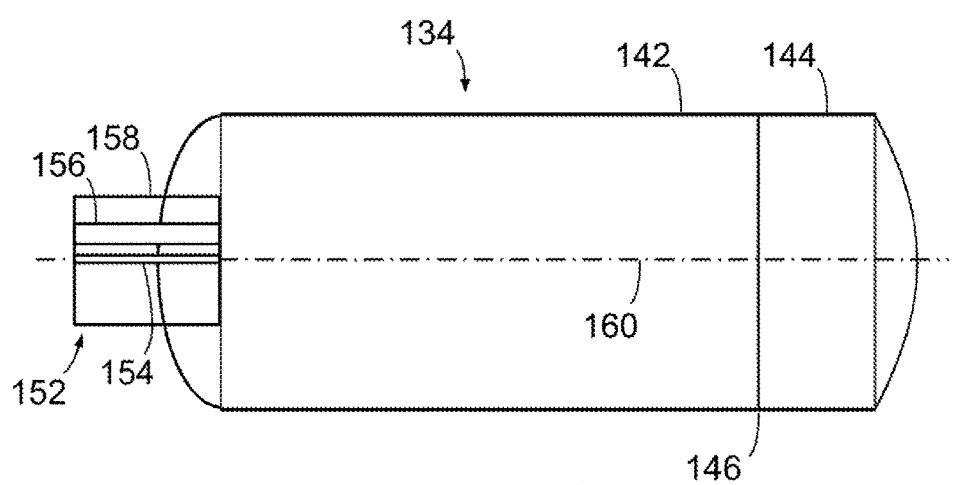
FIG. 28 is a schematic view of a many core fibre system according to an embodiment of the present invention.
Figure 29:
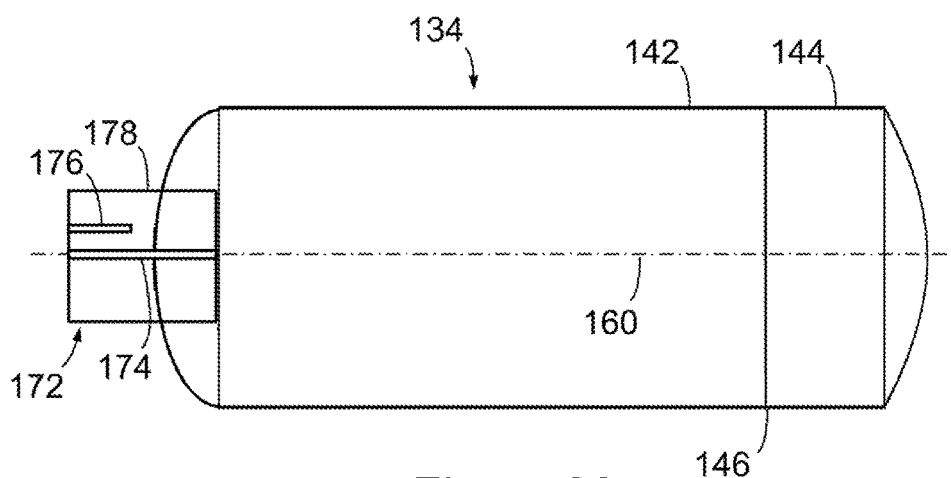
FIG. 29 is a schematic view of a many core fibre system according to another embodiment of the present invention.

FIGS. 28 and 29 are schematic views of multi-core optical systems 150, 160 according to this fourth group of embodiments. Each includes a lens group comparable to lens group 134 of FIG. 27, and like reference numerals have been used to identify like features.

Referring to FIG. 28, multi-core optical system 150 includes an optical fibre 152 and a lens group 134. Optical fibre 152 includes a central, one-moded core 154, which provides the main imaging channel. Imaging performed with central core 154 can produce very sharp axial resolution, with the result that locating features of interest in the specimen can be difficult. Hence, optical fibre 152 also includes one or more offset, very low NA single mode or few moded 'navigator' cores 156 that provide a navigation channel with coarse axial resolution. The cores 154, 156 are surrounded by fibre cladding 158. Hence, imaging through navigator core 156 can make the finding of features of interest easier; once these features in the specimen are found by the user, the system can switch to imaging through main imaging core 154. This switching can be done by providing the microscope or endoscope in which the optical system 150 is provided with separate photodetectors for the outputs of the two cores 154, 156, and switching between these photodetectors as inputs of, for example, a display on which the resulting images of the specimen are displayed to the user. Although navigator core 156 is displaced sideways from optical axis 160, its low numerical aperture means that this notional imperfection does not seriously diminish the system's confocal performance. Navigator core 156 is displaced sideways:

i) Far enough from the optical axis 160 that it does not significantly change the guiding properties of the central core 154, through evanescent field coupling between the two cores 154, 156; but ii) Near enough to the optical axis 160 that comatic aberration due to the sideways offset does not overly mar the confocal performance of navigator core 156.

Referring to FIG. 29, multi-core optical system 170 includes an optical fibre 172 and a lens group 134, and illustrates a techniques according to this embodiment whereby imaging depth into the specimen can be switched between different values by switching the imaging fibre core and hence to effect coarse imaging depth adjustment. Optical fibre 172 includes a central, main one-moded core 174 and one or more laterally offset cores 176. The cores 174, 176 are surrounded by fibre cladding 178.

In this embodiment, each of the one or more laterally offset cores 176 has an exit tip that is also offset in the z direction (that is, the direction parallel to optical axis 160). Again, the sideways displacement of the separate cores is small enough that the comatic aberration arising from the lateral offset does not overly mar the confocal performance of each offset core 176 but far enough apart to prevent evanescent coupling. The system's imaging depth into the specimen is switched between different values by switching the imaging between the differently axially offset cores 176.

Lens group 134 is designed so that the different axial offsets can be accommodated without serious loss of confocal performance. For example, the lower NA designs of Table 1 (Uncorrected 040 026 or Uncorrected 047 030) have performance that is highly insensitive to the fibre tip's axial position, so the imaging depth can be controlled by adjusting the separation between core tip and substrate. Greater depth control can be afforded by use of lower magnification, lower NA systems, as the axial shift in focus is inversely proportional to the square of the system's linear magnification. For low magnification systems, single mode fibre cores outputting fields of correspondingly higher Petermann II NA are employed to maintain a constant optical performance.

A fifth group of embodiments of the present invention employs diffractive lens elements rather than using the aspherical refractive lenses described above. In one such embodiment, a cylindrical glass substrate of dimensions comparable to those of the refractive lenses described above (e.g. approximately 0.5 mm in diameter×2 mm to 3 mm in length) is mounted onto the end of the scanning fibre. A diffraction grating is mounted onto the other end of the cylindrical substrate from the fibre and the whole assembly scanned in the same way as the refractive lens described above. FIG. 30A is a schematic view of such an optical system 180, comprising a scanning optical fibre 182, a scanned cylindrical glass substrate 184 and a holographic (diffraction grating) lens 186 located on the distal end 188 of cylindrical substrate 184.

The fibre output field diffracts through cylindrical substrate 184 from tip of optical fibre 182 onto the proximal surface of diffraction grating lens 186 (much as it does in diffracting from the fibre tip to the aspheric surface of the embodiments of FIGS. 2A to 3), where it is focussed into the specimen by diffraction grating lens 186 (rather than by an aspheric refractive surface).

FIG. 31 includes a schematic side view of optical system 180 (shown in elevation, with dimensions, diffraction grating plane 190 and focal plane 192 indicated) and a view of diffraction grating lens 186, which is a diffraction grating lens of the type that might be most readily used either for reflection mode imaging (wherein fluorescence and driving wavelengths are the same) or in the many-photon fluorescence and the non-descanned systems, where an uncompensated grating is expected to be of low cost and highly practicable.

However, one of the major problems in using a grating lens is its high sensitivity to wavelength; the focal point at the drive wavelength will typically be many tens of microns further from the grating than the focal point at the fluorescent wavelength. For one photon or descanned many-photon fluorescence applications, the grating's wavelength dependence is a significant problem. For example, in a one-photon confocal application with a driving wavelength $\lambda_D$=488 nm and a fluorescence peak wavelength of $\lambda_F$=532 nm, and where a holographic lens focuses the drive light at an axial distance of 1 mm from the plane of the grating lens, then the fluorescence wavelength can be expected to focus at a distance 488/532 mm from the lens plane, i.e. a distance of 83 µm from the drive wavelength focus. This amount of chromatic shift will thwart all confocal imaging schemes.

Figure 32:
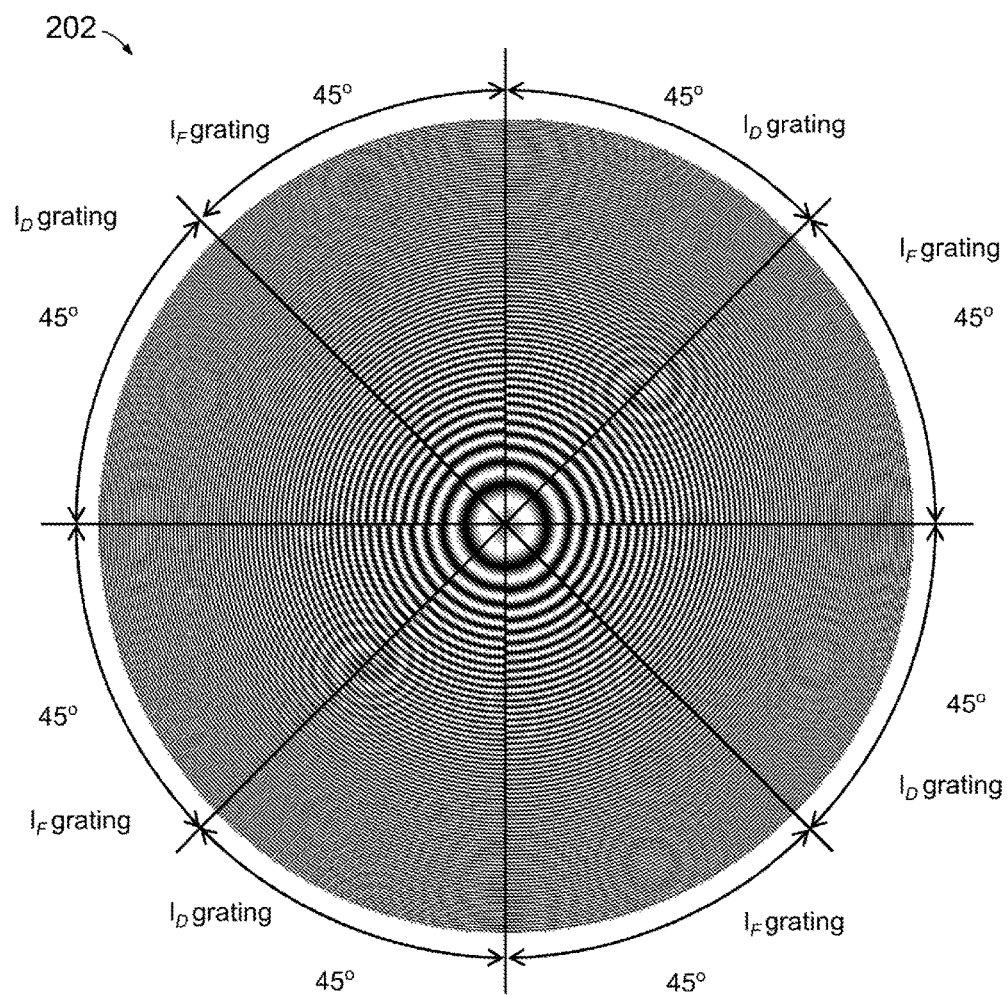
FIG. 32 is a schematic view of the sectored holographic (grating) lens of the optical system of FIG. 30B, in which a half grating is devoted to focussing drive light, the other half to focussing fluorescent light.

However, if half of the holographic lens is given over to a grating that focuses the drive light and the other half to one focussing the fluorescence light, then the two system foci can be brought back to the same point. FIG. 30B is a schematic view of an optical system 200 that includes such a 'compensated' diffraction grating lens 200, but which is otherwise comparable to optical system 180 of FIG. 30A. FIG. 32 is a view of compensated diffraction grating lens 200, in which the diffraction grating is divided into eight 45° sectors, with every second sector (each labelled "$I_D$ grating") comprising a grating that focuses 488 nm light at a point an axial distance of 1 mm from the plane of the grating lens, whereas all the other sectors (each labelled "$I_F$ grating") are given over to gratings that do likewise for 532 nm light. There are abrupt grating discontinuities at the sector edges.

Figure 33:
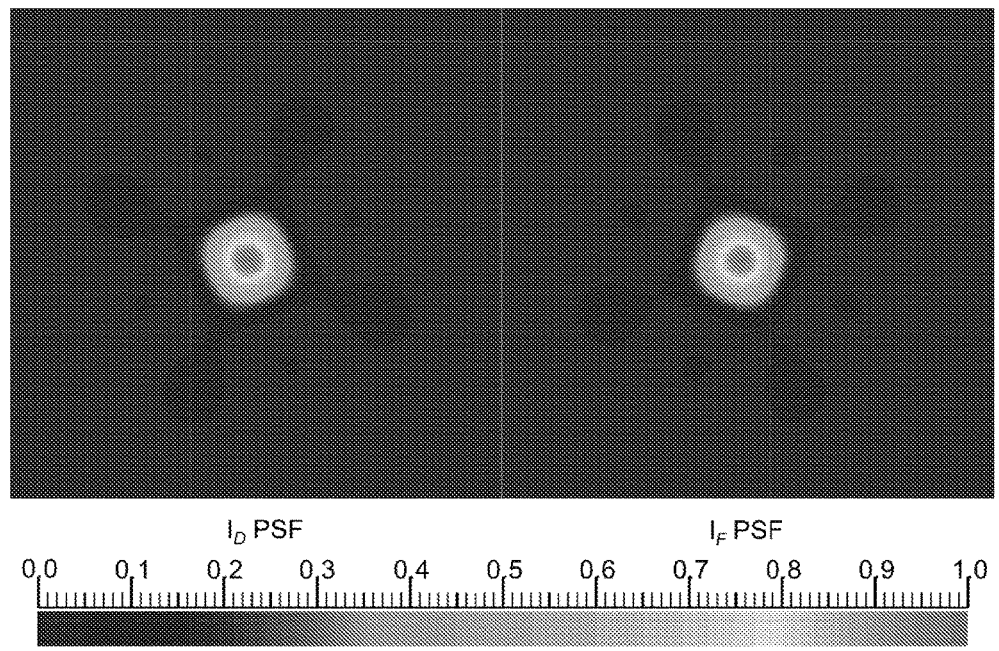
FIG. 33 is a schematic view of the focal plane point spread function for the sectored grating of FIG. 32 for (left) 488 nm driving wavelength (right) 532 nm fluorescence wavelength.
Figure 34:
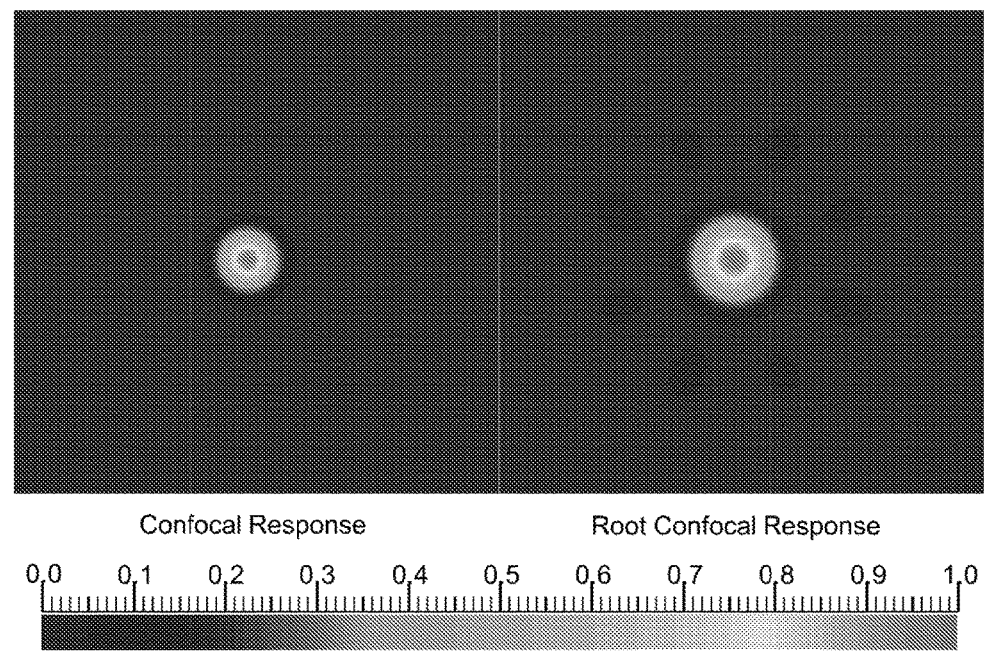
FIG. 34 is a schematic view of the focal plane confocal response for the sectored grating of FIG. 32 with 488 nm driving and 532 nm fluorescence peak wavelength, including (left) the confocal response for subresolvable fluorophore, and (right) the square root of confocal response.

FIG. 33 includes views of the focal plane point spread function for a sectored grating (such as grating 202) for (left register) 488 nm driving wavelength and (right register) 532 nm fluorescence wavelength. Both images have a sidelength of 12.4×12.4 µm. The colour key is in arbitrary units. FIG. 34 includes views of the focal plane confocal response for a sectored grating with 488 nm driving and 532 nm fluorescence peak wavelengths. The left register shows the confocal response for subresolvable fluorophore, while the right register shows the square root of confocal response. Both images have a sidelength of 12.4×12.4 micron, and the colour key is again in arbitrary units. The full width at half maximum lateral resolution is 1.2 µm.

When the sector angles are of 45°, as in the example of FIG. 32, the Strehl ratio for both driving and fluorescence wavelengths is roughly 0.25, since half the grating's area is given to each wavelength and so the peak amplitude of the focussing field is roughly one half what it would be if the whole grating were perfectly tuned to a single wavelength. Therefore, optical system 200 suffers roughly a 12 dB sensitivity loss relative to the refractive systems described above. However, the diffractive solution may be a useful, low cost alternative in some applications. Moreover, one can change the fraction of the grating's surface devoted to each wavelength, so that the fluorescence grating is of greater area than the driving light grating, and the loss of driving wavelength focal intensity can then be compensated for by a higher driving light power, or vice versa.

Active Alignment

According to the above-described embodiments of the present invention, there is also provided an active alignment method, whereby an optical fibre and a lens group (such as optical fibre 12 and lens group 14 of FIGS. 2A and 2B) can be aligned. Broadly, the optical fibre is placed in an alignment jig that allows the relative position and orientation of the optical fibre and lens group to be adjusted while excitation light is input into the optical fibre and output light from the lens group is directed into a suitable light detector (such as a wavefront sensor, astronomer's star test apparatus or interferometer). The relative position and orientation are then adjusted until the least-aberration optimal relative position and orientation is obtained, at which point the optical fibre is bonded to the lens group.

Figure 35:
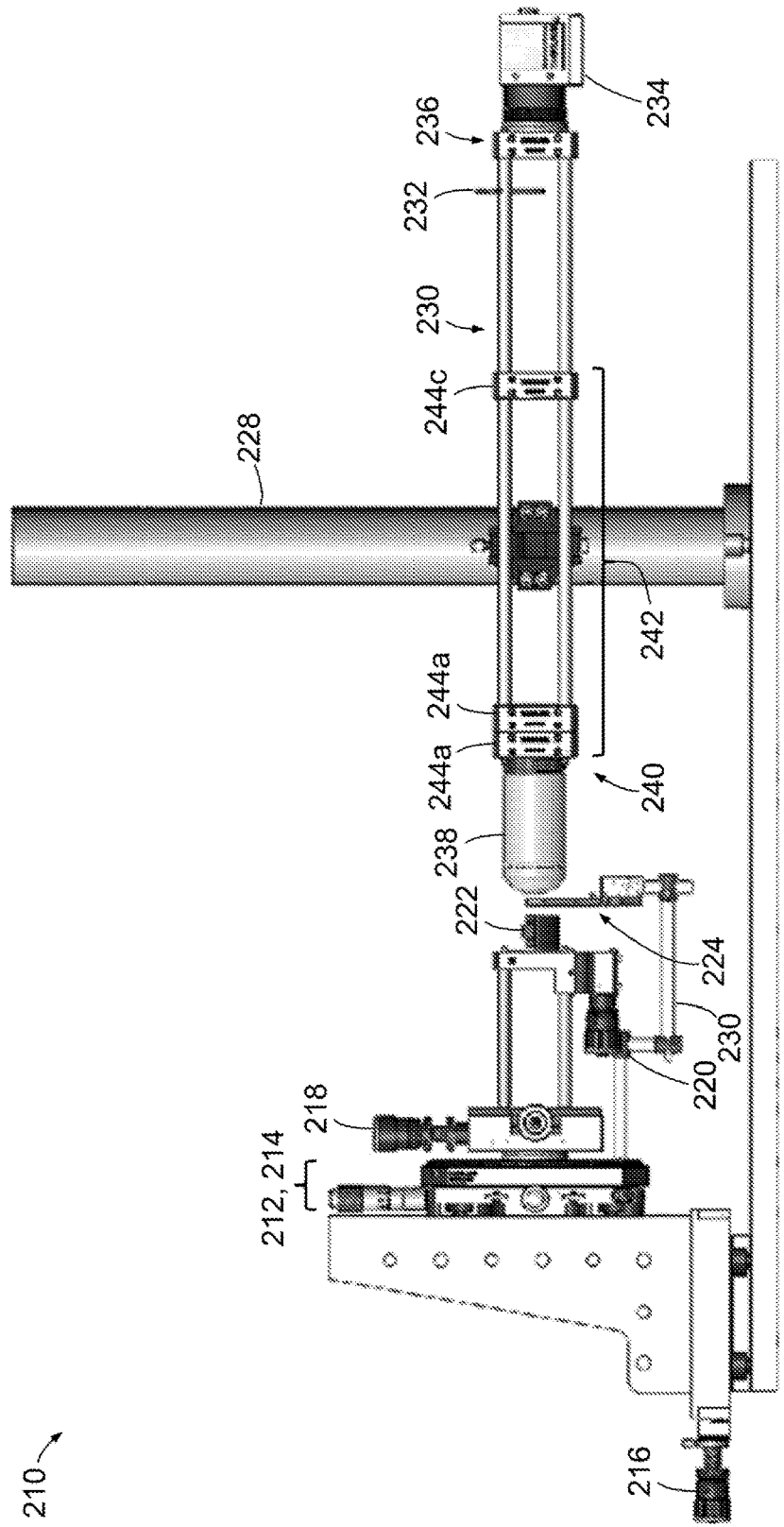
FIG. 35 is a schematic view of an active alignment apparatus according to an embodiment of the present invention.

FIG. 35 is a view of an active alignment apparatus 210 according to an embodiment of the present invention, adapted to align optical systems of the embodiments described above. Alignment apparatus 210 includes an overall X, Y translator 212, a overall rotator 214, an overall Z translator 216, a relative X, Y translator 218 and a relative Z translator 220. Alignment apparatus 210 also includes a fibre clamp 222 mounted on relative Z translator 220, a lens clamp 224 mounted on an arm 226 extending from overall rotator 214 (and including a spring for holding a coverslip in place), a vertical post 228, a horizontal rail 230 (for supporting, and allowing the translation in the z direction of, various components, and itself supported by post 228), a removable rough alignment target 232 on rail 230, and a light detector 234 located at the distal end of rail 230. Alignment apparatus 210 optionally includes an ND Filter 236 (in case attenuation is needed), located optically in front of light detector 234.

Light detector 234 may be in any suitable form, such as a wavefront sensor, a self referencing interferometer (such as a point diffraction interferometer) or a CCD camera (with high enough resolution to view a nearly collimated point spread function spread over at least a 50×50 pixel grid and the ability to linearly measure relative intensities, i.e. with no autogaining, so that a given brightness in the image reproducibly corresponds to the same intensity of light). In this embodiment, light detector 234 is in the form of a Hartmann Sensor.

Overall rotator 214 allows a user to rotate an optical fibre that is held in fibre clamp 222 and lens group held in lens clamp 224 about a horizontal axis, while keeping the relative positions of the fibre and lens group fixed. Overall X, Y translator 212 and overall Z translator 216 allow the user to translate the rotating clamped fibre and lens group in any direction while keeping the relative positions of the fibre and lens group fixed. Relative X, Y translator 218 and relative Z translator 220 allow the user to adjust the relative positions of the input fibre and the lens group.

Alignment apparatus 210 further includes a high numerical aperture collimating objective 238 mounted at the proximal end 240 of rail 230, and a variable Galilean telescope 242 for matching the collimated output beam width from collimating objective 238 to the measurement area of light detector 234.

Galilean telescope 242 comprises a plurality of individual lenses, located in sliding lens holders 244a, 244b, 244c mounted on rail 230. Calibration of alignment apparatus 210 is performed by choosing the lens powers of these lenses that will match the collimated output beam width from collimating objective 222 to the measurement area of light detector 234, then loading the lenses thus identified into Galilean telescope 242, and setting the theoretical axial separation between these lenses by positioning lens holders 24. Most distal of these lenses is a biconvex lens (in lens holder 244c), whose power and axial position on rail 230 are selected to provided the desired zoom of Galilean telescope 242.

The active alignment workflow is as follows:
i) The optical fibre and lens group are loaded into the fibre clamp 222 and lens clamp 224, respectively;
ii) The tip of the optical fibre is brought to within 10 μm of the proximal surface of the lens group using relative Z translator 220;
iii) A roughly correct sideways (X, Y) position of the optical fibre is set with the aid of a plan viewing microscope (not shown) by adjusting the X position with relative X, Y translator 218 for a central-by-sight X-position of the lens, then rotating the fibre-lens group assembly through a 90°, then adjusting the Y position with relative X, Y translator 218 for a central-by-sight Y-position, then rotating back;
iv) Steps ii and iii are repeated if needed until the user deems the fibre to be centred by sight and within 10 μm of the proximal surface of the lens group;
v) The optical fibre is powered with about 1 mW of the driving wavelength light;
vi) The X, Y and Z positions are adjusted with overall X, Y and Z translator 212 to illuminate light detector 234 to its nominal operating beamwidths (if a wavefront sensor or interferometer is used) or for the maximum peak intensity in the point spread function (if a CCD camera is used);
vii) The X and Y positions are adjusted with relative X, Y translator 218 slightly to correct the measured aberration, then step vi is repeated;
viii) Steps vi and vii are repeated until the least overall aberration of the whole system is achieved (correspond to maximum spot brightness if light detector 234 is in the form of a CCD camera);
ix) The lens-fibre assembly is then glued with the help of the plan viewing microscope.

Lens Surface Quality Assessment

According to the above-described embodiments of the present invention, there is also provided a lens surface quality assessment method. Broadly, according to this method, a known diameter pinhole is positioned at the focus of an optical system (according to any of the above described embodiments), the power transmitted through the pinhole is measured, the pinhole is removed so that the total output power can also be measured and then the ratio of the power through pinhole to the total power can be related to the root mean square lens surface roughness.

A rough lens surface splits transmitted light into an unaberrated, but attenuated, part and a randomly sprayed part. The power attenuation coefficient for the unaberrated part is:

$$\Gamma^2 = \frac{P_{unaberrated}}{P_{input}} = \exp\left(-\left(\frac{2\pi\sigma}{\lambda}\right)^2\right) \quad \text{Equation 9}$$

where $\sigma$ is the RMS wavefront error in waves induced by the surface roughness and $\lambda$ is the light's wavelength. A fraction $1-\Gamma^2$ of the input light is converted to the randomly sprayed part, which does not converge to a tight focus. Therefore, a surface roughness quality assurance test grounded on measuring the fraction of light contributing to the tight focus is as follows.

Figure 36:
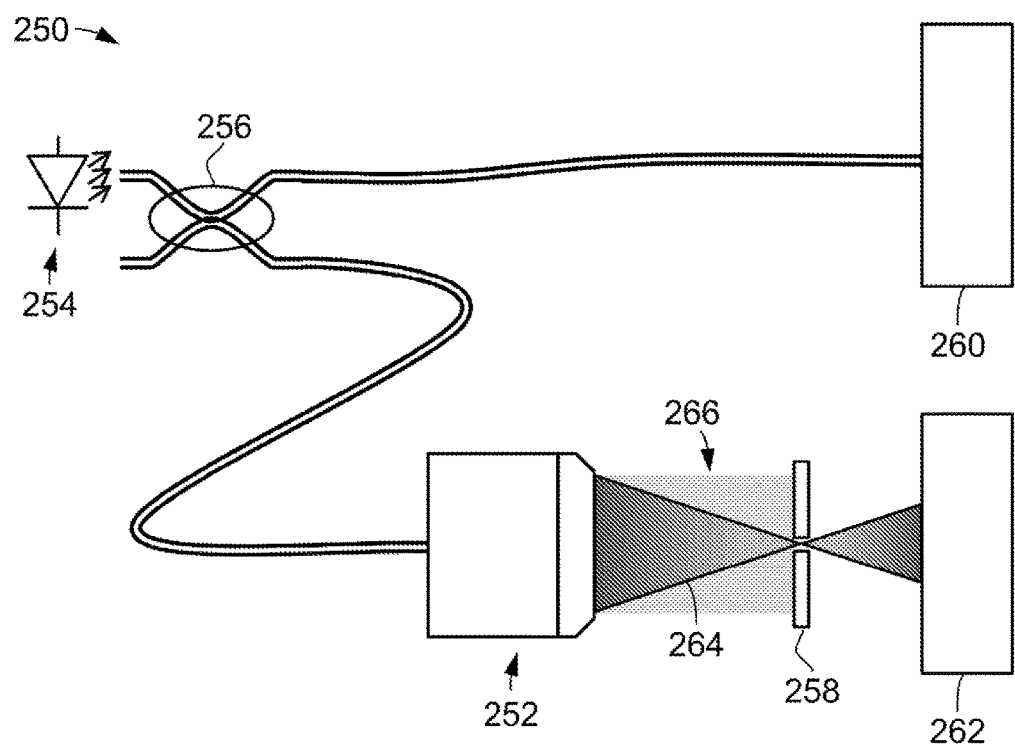
FIG. 36 is a schematic view of surface roughness quality assessment apparatus according to an embodiment of the present invention.

FIG. 36 is a view of a lens surface quality assessment apparatus 250 according to an embodiment of the present invention (shown with a lens or lens group 252 under test), adapted to align optical systems of the embodiments described above. Assessment apparatus 250 includes a laser source 254, an approximately roughly 50-50 directional coupler 256, a withdrawable pinhole 258, a first power measurement head 260 and a second power measurement head 262.

Light from laser source 254 is split by coupler 256 into a reference fibre 264 (that transmits light to first power measurement head 260) and driving fibre 266 that transmits light to lens 252. Some of the light transmitted by lens 252 passes through pinhole 258 and into second power measurement head 262.

As mentioned above, a rough lens surface splits transmitted light into a focussed part (which is unaberrated, but attenuated) 264 and a randomly sprayed part 266.

The precise split ratio of coupler 256 is not important, and appreciable light levels at the outputs of reference fibre 264 and driving fibre 266 are all that is needed. Alternatively, a beam splitter can be used to split light into a reference beam and a driving beam. All measurements are taken as the ratio of the power P1 into first measurement head 260 and the power P2 into second power measurement head 262; P1 and P2 are measured simultaneously. Desirably this is be done with a trigger signal to both power measurement heads 260, 262 if they are of the type that can be triggered. In principle, with a highly stable laser source 254, with substantially unwavering power output, one could omit coupler 256 and first power measurement head 260, and simply measure absolute power into second power measurement head 262. However, the use of the ratio P2/P1 obtained from triggered simultaneous measurement allows the use of a lower quality, wavering output laser source.

Pinhole 258 is removable and also mounted on an XYZ translation stage (not shown). The translation stage is adjusted to the aperture of pinhole 258 at the focus of lens 252, i.e. at the position that gives peak power into second power measurement head 262. This peak power, as a ratio of measurement of the ratio of P2 to P1, is recorded and then pinhole 258 is withdrawn. The power into second power measurement head 262, recorded as the ratio of P2 to P1, is again measured. The ratio of the measurement with pinhole 258 installed to that without pinhole 258 is the final experimental result used as a measure of lens quality.

Figure 37:
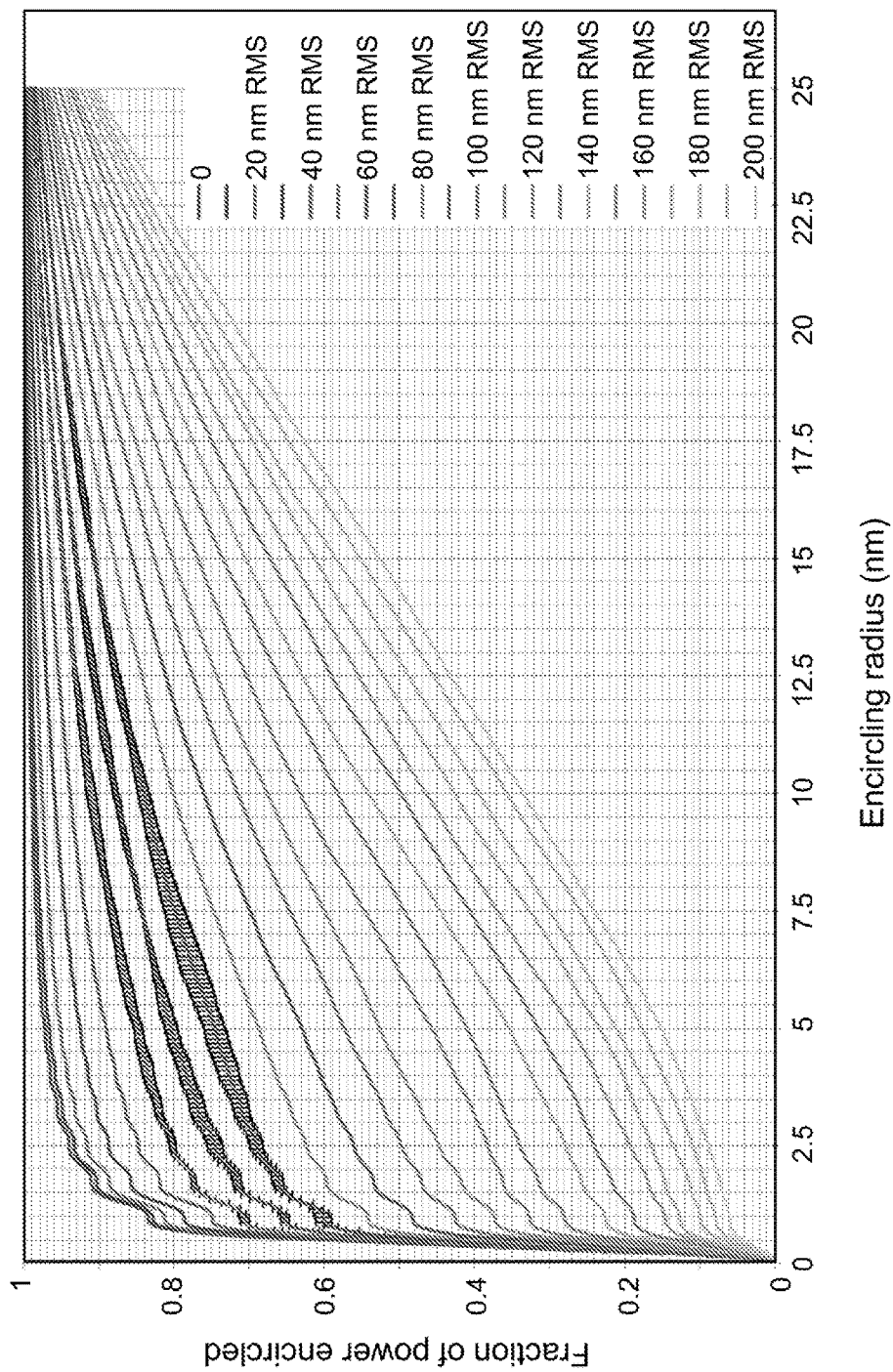
FIG. 37 is a schematic view of encircled energy as a function of encircling radius for 0.3 NA according to an embodiment of the present invention.

For a given diameter pinhole and lens numerical aperture, the RMS surface roughness can be calculated from the final QA metric. FIG. 37 is a plot, for surface roughnesses from 0 to 200 nm RMS in 10 nm steps, of the calculated fraction of the total power flowing through the focal plane that is encircled by a circular hole in the focal plane centred on the focus itself as a function of encircling radius in nm. In case the correspondence between RMS surface roughness and curve in unclear from the figure, it should be noted that the curves correspond in vertical sequence to the sequence of surface roughness values indicated on the right of the plot.

The curves were calculated by the numerical integration of the full Maxwell equations describing the propagation of light through a 0.3 NA lens with surface roughness. Each encircled energy curve is the average curve of those gotten for five Monte Carlo simulations. Also shown are 98% two-sided confidence error bars for the 50 nm, 60 nm and 70 nm RMS surface roughness curves. For a given encircling radius in FIG. 37, a plot of the value of each curve in FIG. 37 at that radius as a function of the RMS surface roughness yields a calibration curve for assessment apparatus 250 of FIG. 36 when a pinhole 258 with this given radius is used and when the lens output is a 0.3 NA field.

Figure 38:
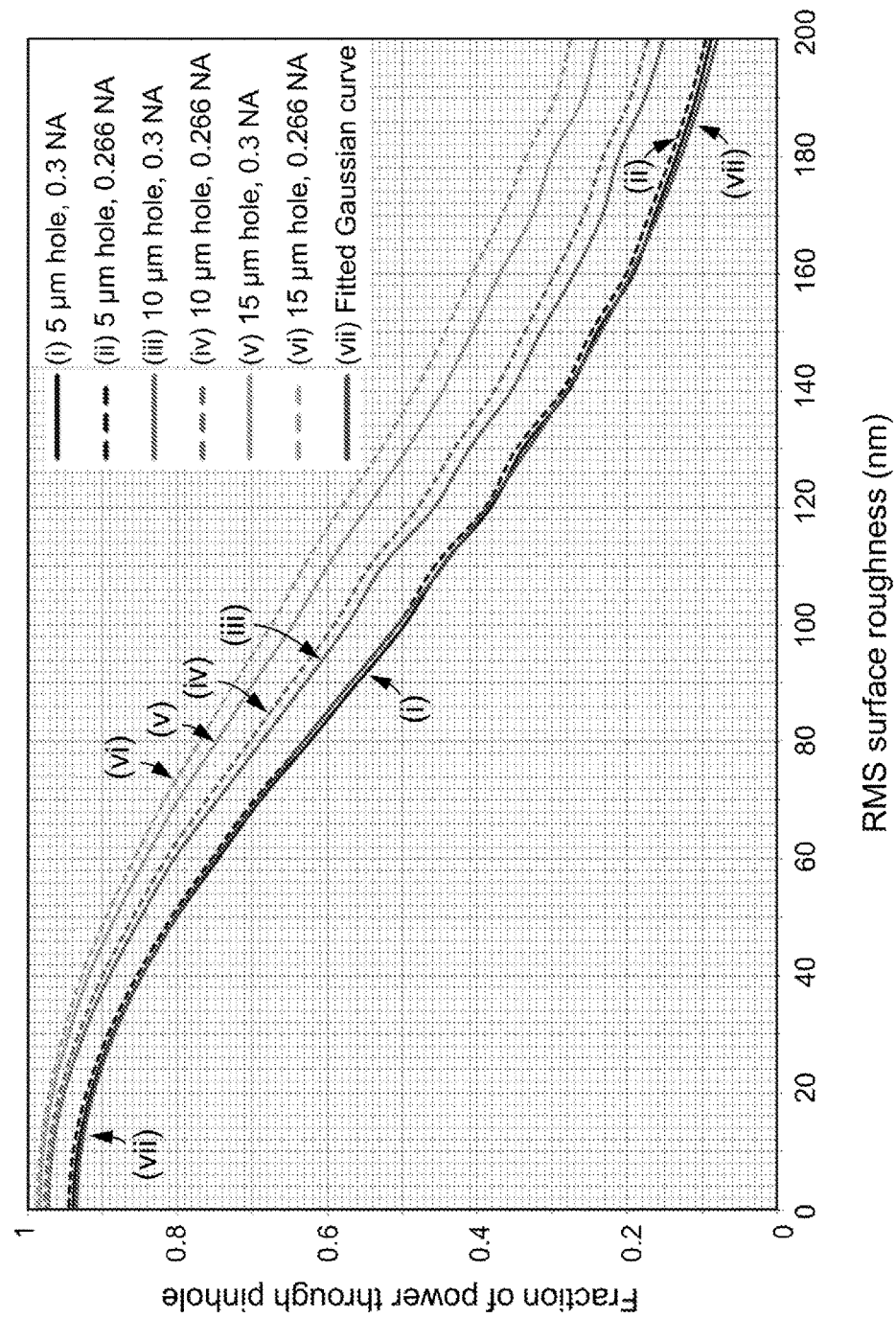
FIG. 38 is a schematic view of peak fraction of power through pinhole in the quality assessment apparatus of FIG. 36 as a function of RMS lens surface roughness.

FIG. 38 is such a plot, i.e. of the fraction of the lens's total power output that can pass through pinhole, when pinhole position is adjusted for peak power throughput, as a function of RMS surface roughness in nm, for pinholes of diameters 5 μm, 10 μm and 15 μm and for both a 0.3 NA lens and a 0.266 NA lens.

It can be seen that the fractions plotted in FIG. 38 are not highly sensitive to either the exact pinhole diameter nor to the field numerical aperture, especially at a 5 μm pinhole diameter. Thus it would seem from these results that assessment apparatus 250 of FIG. 36 should yield a credible measurement of surface roughness. A least squares best fit Gaussian curve for the 5 μm pinhole results is also shown in FIG. 38. Thus it can be seen that a good working estimate of the lens's RMS surface roughness is given by:

$$\sigma = 128.0\sqrt{-\log_e(1.070 f)} \qquad \text{Equation 10}$$

where f is the fraction measured in the test and σ is in nanometers, when a 5 nm diameter pinhole is used. The relationship of Equation 10 is the inverse of the Gaussian least squares best fit curve:

$$f = 0.935 \exp\left(-\left(\frac{2\pi \times 0.608 \times \sigma}{\lambda}\right)^2\right) \qquad \text{Equation 11}$$

shown in FIG. 38. The spread of the light over the focal plane as shown in FIG. 37 does depend somewhat on the surface roughness's statistical properties (particularly correlation length), but Equation 11 is almost the same as the power fraction of Equation 9. Indeed, a fair estimate of the surface roughness can be gotten by simply using the inverse of the power fraction formula in Equation 9. This means that, for a 5 μm diameter pinhole and a 0.3 NA lens, the power through the pinhole is the fraction of power being focused by the rough lens. The 5 μm diameter pinhole is a good discriminator between the focused light 264 and sprayed light 266, and thus Equation 10 is likely to be only very weakly dependent on the distribution of the sprayed light in the focal plane; all that matters is that sprayed light 266 should fall outside the aperture of pinhole 258. Therefore, Equation 10 is a robust way to infer lens surface roughnesses from the tests performed with assessment apparatus 250 of FIG. 36.

Figure 39A:
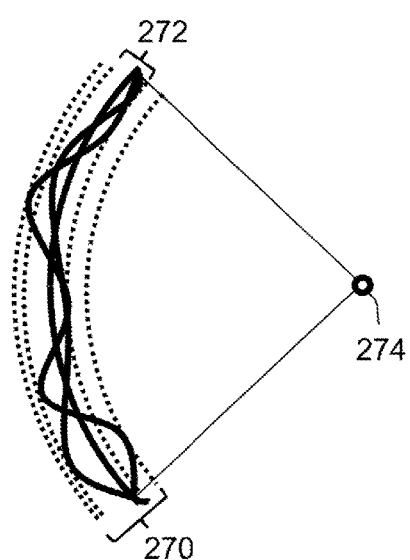
FIGS. 39A and 39B are schematics view of acceptable and unacceptable aberration specifications, respectively, illustrating how aberration specifications must be met at the same nominal focal point for both excitation and fluorescence wavelengths.
Figure 39B:
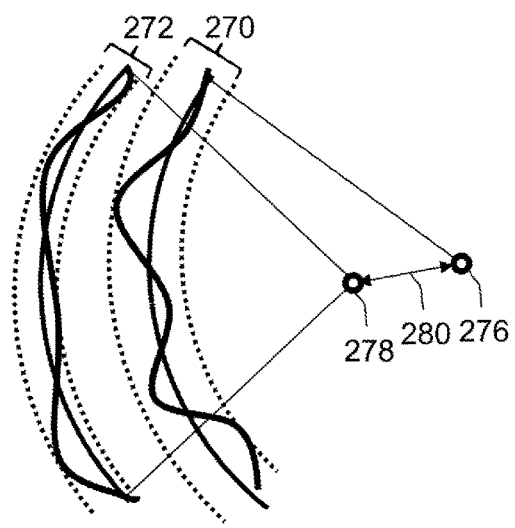

Appendix 1: Combined Strehl Ratio/Chromatic Aberration Specification for In-Vivo Imaging Systems One way to combine the Strehl and chromatic shift specifications is through the thought experiment depicted schematically in FIGS. 39A and 39B, which compares acceptable (FIG. 39A) and unacceptable (FIG. 39B) definitions of aberration. An acceptable definition of aberration is one in which aberration specifications are met at the same nominal focal point for both excitation and fluorescence wavelengths. IN FIGS. 39A and 39B, for λ=488 nm the wavefront and RMS error <0.05 are shown at 270, and for λ=532 nm the wavefront and RMS error <0.05 are shown at 272. In FIG. 39A, the same nominal focal point is chosen to measure aberration at λ=488 nm and λ=532 nm (indicated at 274). In FIG. 39B, different nominal focal points are is chosen to measure aberration at λ=488 nm and λ=532 nm (indicated at 276 and 278 respectively); the displacement between focal points 276, 278 is a measure of chromatic shift 280.

The combined specification can be used to clearly visualise the detrimental effect of chromatic aberration on in vivo systems. The example of FIGS. 39A and 39B is for one-photon fluorescence confocal imaging with a drive wavelength of 488 nm and a fluorescence peak of 532 nm, but the principles apply to any pair of drive and fluorescence wavelengths.

Referring to FIG. 39A, in this thought experiment, with the lens system in an interferometer lit so as to get the desired output NA and desired imaging point, the best focus is found for one of the wavelengths. The Strehl ratio is measured. Then, without adjusting the interferometer in any way, the wavelength of the source is changed to the other wavelength, and the Strehl ratio remeasured. The product of these two Strehl ratios defines the instrument's sensitivity.

In this thought experiment, the tester can re-focus the interferometer to a different nominal focus and repeat the above measurement to see whether a better result can be gotten. When the focus is found so that no refocus will give further reduction in the Strehl ratio product, this minimum result is the combined specification and, moreover, the final nominal focus defines a point on the focal surface.

It should be noted that, because no interferometer adjustment between the measurement of the two Strehl ratios is made, the allowable chromatic shift specifications, both axial and sideways (colour registration), are implicit in this specification. In contrast, the "unacceptable measurement" method illustrated in FIG. 39B allows an adjustment between the two Strehl ratio measurements. This technique would give an explicit measurement of the chromatic shift. The chromatic shift is equal to the displacement between the two in general different focuses that separately optimise the Strehl ratios at the drive and fluorescence peak wavelengths.

Thus, if δ(r, λ) is the Strehl ratio in the object space at the position with position vector r when the system is driven at wavelength λ, the optimum Strehl ratio at that wavelength is $$\max_{r \in \mathbb{R}^3} \delta(r, \lambda) \qquad \text{Equation 12}$$

and the "focus" at this wavelength is the position $r_{max}$ that achieves it. The optimum Strehl product specification for the lens system is then:

$$\max_{r \in \mathbb{R}^3}(S(r, \lambda_D) \times S(r, \lambda_F)) \quad \text{Equation 13}$$

where $\lambda_D$ is the drive wavelength and $\lambda_F$ the fluorescence peak wavelength i.e. it is the product that is maximised and used as the specification, not the product of the maximum Strehl ratios for the individual wavelengths. The confocal system focus is the position r that achieves this maximum Strehl product.

Indeed, one can define a total aberration loss, being:

$$L_A = -10\log_{10}[\max_{r \in \mathbb{R}^3}(S(r, \lambda_D) \times S(r, \lambda_F))] \text{ dB} \quad \text{Equation 14}$$

and also a chromatic aberration loss:

$$L_C = -10\log_{10}\left[\frac{\max_{r \in \mathbb{R}^3}(S(r, \lambda_D) \times S(r, \lambda_F))}{\max_{r \in \mathbb{R}^3}(S(r, \lambda_D)) \times \max_{r \in \mathbb{R}^3}(S(r, \lambda_F))}\right] \text{ dB} \quad \text{Equation 15}$$

which is the ratio of the optimum Strehl product to the product of the optimum Strehls. The potential aberration loss:

$$L_P = -10\log_{10}[\max_{r \in \mathbb{R}^3}(S(r, \lambda_D)) \times \max_{r \in \mathbb{R}^3}(S(r, \lambda_F))] \text{ dB} \quad \text{Equation 16}$$

is the aberration loss that could be achieved if there were no chromatic shift in the system. If there is no chromatic shift, the product of the optimum Strehls is the same as the optimum Strehl product and the confocal system focus as well as the focuses at the two separate wavelengths are the same point. In general, the total loss is always greater than the potential loss and:

$$L_A = L_C + L_P \text{ with } L_C \geq 0 \quad \text{Equation 17}$$

It should be noted that this thought experiment is used to define the focal surface as the locus of all minimum Strehl ratio product points that correspond to all the possible imaging positions, which change as the illumination point is scanned on the imaging surface.

For a many-photon system, the above idea is used, but the Strehl ratio is raised to the power of the photon fluorescence process order for the drive wavelength (i.e. raised to the power N). The fluorescence wavelength Strehl ratio is replaced by unity if the system is not descanned (i.e. if α=0). Thus, for example, for descanned two-photon imaging:

$$L_A = -10\log_{10}[\max_{r \in \mathbb{R}^3}(S(r, \lambda_D)^2 \times S(r, \lambda_F))] \text{ dB} \quad \text{Equation 18}$$

$$L_C = -10\log_{10}\left[\frac{\max_{r \in \mathbb{R}^3}(S(r, \lambda_D)^2 \times S(r, \lambda_F))}{\max_{r \in \mathbb{R}^3}(S(r, \lambda_D)^2) \times \max_{r \in \mathbb{R}^3}(S(r, \lambda_F))}\right] \text{ dB}$$

$$L_P = -10\log_{10}[\max_{r \in \mathbb{R}^3}(S(r, \lambda_D)^2) \times \max_{r \in \mathbb{R}^3}(S(r, \lambda_F))] \text{ dB}$$

Appendix 2: General Definition of the Numerical Aperture of a Focussing Electromagnetic Field In this document, the following definition for the numerical aperture of a focussing optical field has been used. It is based on the idea of the Petermann II definition of the radius of the focal plane spot, which is a proven method for measuring the radius of a single mode fibre's eigenfield using only farfield intensity measurements.

Figure 40:
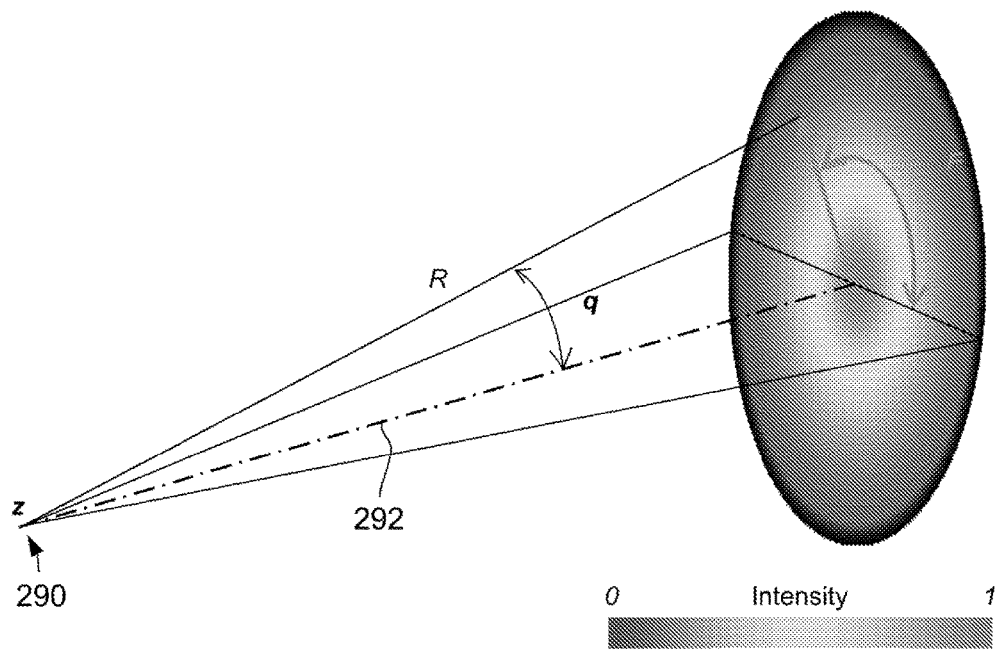
FIG. 40 is a schematic view of co-ordinates for the Petermann II definition of NA, as employed herein.

FIG. 40 is a view of a lightcone radiated from a focus 290 with an optical axis 292 and casting a farfield intensity pattern on a spherical shell of radius R (big enough that the electromagnetic field has reached farfield behaviour at this radius from the focus) centred on the focus. The co-ordinates on the farfield shell are modified spherical polar co-ordinates: the longitudinal angle φ and the normalised optical radius ρ, which, in a vacuum is the sine of the latitudinal angle θ made by a ray joining the point in question to the focus and the optical axis. If the focus is in a material of refractive index n then:

$$\rho = n \sin\theta \quad \text{Equation 19}$$

The physical radius in a conventional cylindrical polar co-ordinate system diverges to infinity as the normalised radius approaches the medium's refractive index (i.e. approaches unity in a vacuum).

Given these definitions, the Petermann II Numerical Aperture is:

$$NA_{Petermann\,II} = \sqrt{2}\sqrt{\frac{\int_0^n \int_0^{2\pi} I(\rho, \phi)\,d\phi\rho^3\,d\rho}{\int_0^n \int_0^{2\pi} I(\rho, \phi)\,d\phi\rho\,d\rho}} \quad \text{Equation 20}$$

where $I(\rho, \phi)$ is the farfield intensity, i.e. power flux through unit area at each point on the spherical shell, as a function of the modified co-ordinates.

This definition requires the intensity distribution's centroid to lie on the optical axis. If not, one must calculate the centroid's position vector and re-align the co-ordinate axes so that the optical axis passes through the centroid.

This definition of the numerical aperture has the following properties:
i) It reduces to the wanted definition of the numerical aperture, that is, the sine of the illumination cone's half angle when the fields are unapodised, i.e. when the spherical shell is uniformly lit inside the clear aperture; and
ii) It fulfils a Heisenberg inequality, that is:

$$r_2 NA_{Petermann\,II} \geq \frac{\lambda}{\sqrt{2}\pi} \quad \text{Equation 21}$$

In the inequality, $r_2$ is the radius of gyration about the optical axis of the intensity point spread function i.e.:

$$r_2 = \sqrt{\frac{\int_F r^2 I\,dA}{\int_F I\,dA}} \quad \text{Equation 22}$$

where l is the intensity the focal plane, r the distance from the optical axis 292 and the surface integral is done over the whole focal plane F). Equality holds if and only if:
i) The point spread function (and therefore the farfield distribution) is Gaussian with zero phase (corresponding to zero aberration for a field focussed in freespace); and ii) The Gaussian spotsize is independent of direction i.e. the field distributions are radially symmetric (independent of azimuthal angle).

Thus, the Petermann II radius measures the potential lateral resolution of an exit pupil field when aberration is absent. The properties above make for an excellent characterisation of an apodised system's potential resolving power and the new definition reduces to the normal one in non-apodised conditions and thus this is the definition exclusively used by Optiscan.

Figure 41:
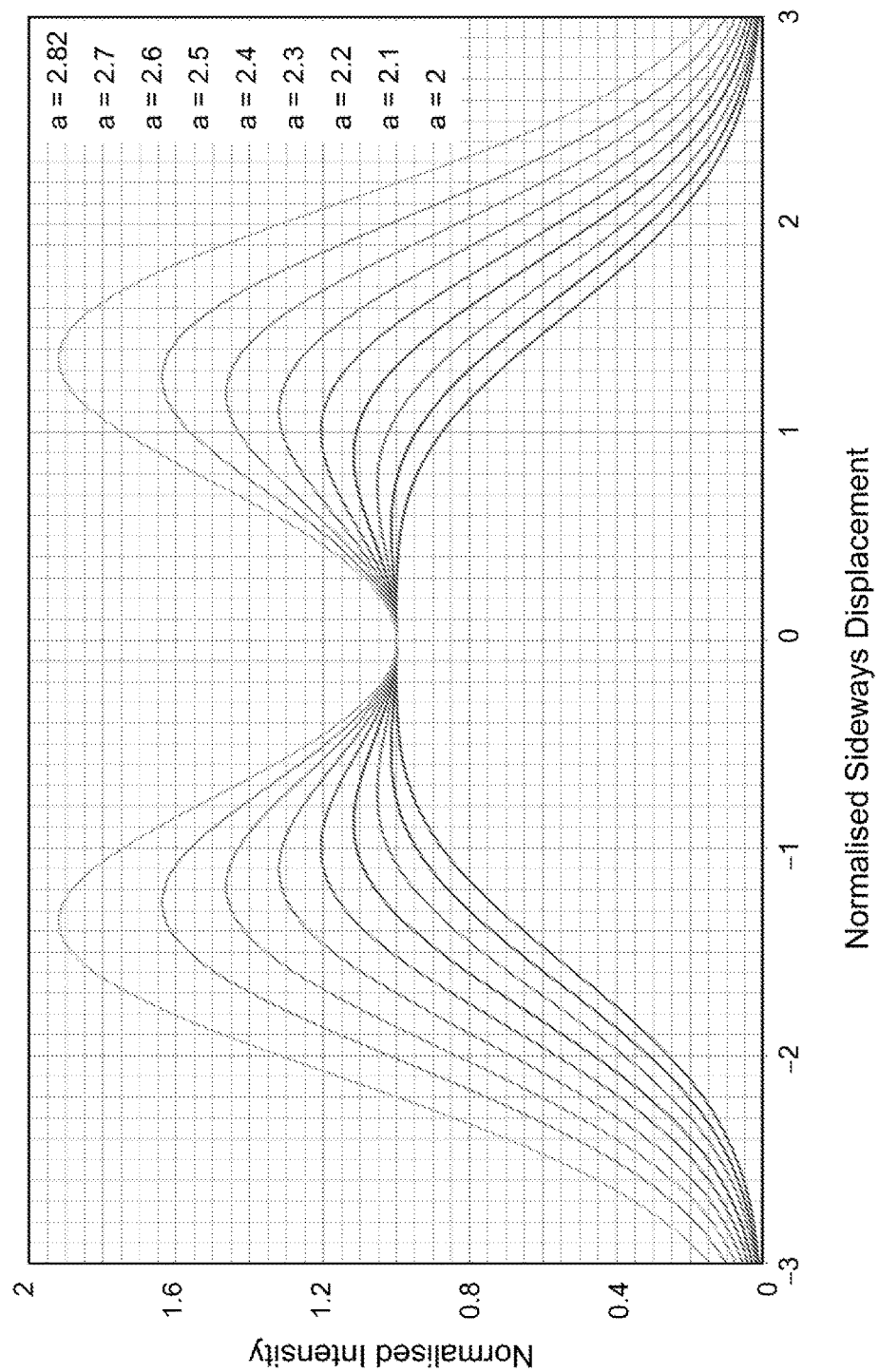
FIG. 41 is a plot indicating the resolvability of two Gaussian spots by plotting normalised intensity against normalised sideways displacement for various spot separations.

For Gaussian focal spots, i.e. ones where the field amplitude is proportional to $\exp(-r^2/(2\,\sigma^2))$ the radius of gyration is a and the mode field diameter is $2\sqrt{2}\sigma \approx 2.8\,\sigma$. If two Gaussian beams of the same spotsize and power are spaced varying distances apart, the beam intensity as a function of sideways displacement x from their midpoint along the line joining the two spot focuses is as shown in FIG. 41, which indicates the resolvability of two Gaussian spots by plotting normalised intensity against normalised sideways displacement for various spot separations in terms of $a \times \sigma$. The values of a are indicated in the figure, and correspond to the intensity curves in sequence from top to bottom (such that the uppermost curve in the figure corresponds to a=2.82 and the lowermost curve to a=2).

The displacement on the horizontal axis is normalised so that $\sigma=1$. The vertical axis is normalised so that the intensity at the midpoint between the focuses x=0 is unity. When the spots are 1 σ apart, there is no dip in intensity between the spots and they are unresolved. The contrast between the minimum dip and the peak intensity however increases swiftly with separation distances further than 1 σ apart. The Rayleigh criterion for unapodised fields corresponds to a contrast of 26.3% between the brightness of the dip and the peak brightness. For Gaussian fields, FIG. 41 shows that this contrast is achieved at about 2.5 σ, or from Equation 21, when the separation is 0.56 λ/NA. This is remarkably near the Rayleigh resolution for unapodised fields, being 0.61 λ/NA. It would therefore seem reasonable to use $2\sqrt{2}\sigma \approx 2.82\,\sigma$ as the Gaussian resolution, since this is the Petermann II mode field diameter and is widely understood. The brightfield resolution for Gaussian beams following this definition is therefore:

$$\Delta x \geq \frac{2\lambda}{\pi NA_{Petermann\,II}} \quad \text{Equation 23}$$

The N-photon confocal point spread function is the product of the drive wavelength point spread function to the power of N and the fluorescence point spread function. Therefore, in the Gaussian beam case, the confocal point spread function is also Gaussian, and the spotsize is the reciprocal of the sums of all the reciprocal spotsizes for the constituent beams (since the exponents in the Gaussian functions add). Therefore, the confocal resolution of a perfectly chromatically corrected system is:

$$\Delta x \geq \frac{2}{\pi NA_{Petermann\,II}} \frac{\lambda_D \lambda_f}{\sqrt{N\lambda_f^2 + \lambda_D^2}} \quad \text{Equation 24}$$

Modifications within the scope of the invention may be readily effected by those skilled in the art. It is to be understood, therefore, that this invention is not limited to the particular embodiments described by way of example hereinabove.

In the claims that follow and in the preceding description of the invention, except where the context requires otherwise owing to express language or necessary implication, the word "comprise" or variations such as "comprises" or "comprising" is used in an inclusive sense, that is, to specify the presence of the stated features but not to preclude the presence or addition of further features in various embodiments of the invention.

Further, any reference herein to prior art is not intended to imply that such prior art forms or formed a part of the common general knowledge in any country.

The invention claimed is:

1. A lens group for an endoscope or microscope, comprising:
   one or more lens elements, each of uniform refractive index, adapted to:
   i) focus, with high wavefront aberration correction, driving or excitation light received from an exit tip of an optical waveguide located substantially against a proximal surface of the lens group to a point observational field with narrow point spread function beyond a distal surface of the lens group; and
   ii) transmit, with high wavefront aberration correction, fluorescence or reflected return light received by the distal surface from the point observational field back to the exit tip of the optical waveguide at the fluorescence wavelength,
   wherein the lens group has a chromatic shift that is highly corrected such that:
   i) the lens group focuses fluorescence light received from the exit tip of the optical waveguide to the point observational field to within a small margin of error; and/or
   ii) an input light wavepacket of less than a picosecond pulse width and centred at a wavelength of the driving light is only slightly broadened in pulse width when passing through the lens group.

2. A lens group as claimed in claim 1, wherein the fluorescence return light and the driving or excitation light have the same wavelength.

3. A lens group as claimed in claim 1, comprising:
   i) a diffractive optical element located at and constituting the distal surface; or
   ii) a diffractive optical element located at and constituting the distal surface, wherein the lens group comprises a non-focussing glass rod, wherein focussing is provided by the diffractive element.

4. A lens group as claimed in claim 1, wherein the lens group has a chromatic shift that is highly corrected such that the lens group focuses fluorescence light received from the exit tip of the optical waveguide to the point observational field to within a small margin of error, the lens group having resolution and aberration correction criteria such that:
   a) the numerical aperture of light focussed by the lens group is (i) 0.15 or greater when the lens group receives light from the optical waveguide at a nominal driving light wavelength, and (ii) 0.15 or greater at a wavelength of peak fluorescence emission; and
   b) either the product of first and second corresponding Strehl ratios measured at the point observational field is either greater than or equal to 0.5 or the generalised Strehl product:

$$\max_{r\in\mathbb{R}^3}(\mathcal{S}(r,\lambda_D)^N \times \mathcal{S}(r,\lambda_F)^\alpha)$$

is greater than or equal to 0.5, whichever definition is applicable to a fluorescence imaging mode.

5. A lens group as claimed in claim 4, wherein the lens group comprises (i) two unlike glasses in the lens group, (ii) a spherical interface between the two unlike glasses, and (iii) a distal surface that is aspheric, whereby the lens group is adapted for driving/fluorescence wavelength pairs in a broadened seeable light spectrum of wavelength 450 nm to 850 nm.

6. A lens group as claimed in claim 4, comprising a plurality of glasses of more than one type, wherein the lens group has mutually cancelling dispersion and the lens group is adapted for use with any driving/fluorescence wavelength pair in the broadened seeable light spectrum wavelength range of 450 nm to 850 nm.

7. A lens group as claimed in claim 1, wherein the lens group has a chromatic shift that is highly corrected such that an input light wavepacket of less than a picosecond pulse width and centred at a wavelength of the driving light is only slightly broadened in pulse width when passing through the lens group, the lens group having pulse broadening criteria defined such that an input light wavepacket centred at a nominal driving wavelength and of twenty femtoseconds in duration is broadened to a wavepacket at of equal central wavelength and of less than one hundred femtoseconds duration by a multipathing contribution from the lens group.

8. A lens group as claimed in claim 1, comprising one type of glass, wherein the lens group comprises an amount of glass such that transmitted wavefields have insufficient transmit time to disperse to an extent that would produce a Strehl ratio less than 0.5, whereby the lens group is adapted for closely spaced driving/fluorescence wavelength pairs.

9. A lens group as claimed in claim 1, comprising a homogeneous cylindrical rod and a diffraction grating bonded to the distal end thereof, wherein either:
   i) the grating focuses the driving light to the point observational field and guides the return light back from the point observational field into the exit tip of the optical waveguide; or
   ii) the grating focuses the driving light to the point observational field, the grating guides the return light back into the exit tip of the optical waveguide, a first portion of the grating is configured for focussing the driving light and a second portion is configured to collecting the return light.

10. A lens group as claimed in claim 1, comprising a plurality of lens elements glued or otherwise bonded together after manufacture.

11. An optical system, comprising a lens group as claimed in claim 1.

12. An optical system as claimed in claim 11, comprising the optical waveguide.

13. An optical system as claimed in claim 12, further comprising a cantilevered mount configured to hold the optical waveguide, a magnet mounted on the optical waveguide, and:
   i) a drive system for driving the magnet to vibrate in two planes such that the distal surface of the lens groups is scanned at high speed to build up a wide field of view image from the return light; or
   ii) a drive system for driving the magnet to vibrate in two planes such that the distal surface of the lens groups is scanned at high speed to build up a wide field of view image from the return light, the drive system being configured to scan in a first direction with a frequency of at least 500 Hz and scan in a second direction orthogonal to the first direction with a frequency of at least 0.5 Hz, such that an image whose field of view is at least 200 µm×200 µm can be obtained from the return light.

14. An optical system as claimed in claim 11, wherein the optical waveguide further comprises:
   i) one or more auxiliary lightguiding cores, so that the imaging numerical aperture can be switched between the main, high resolution value to a low value, possibly with in-between steps to allow the user to position the image easily, with coarse axial resolution and high tolerance to siting errors and hand unsteadiness and then switch to a high resolution mode once the target tissue has been identified; and/or
   ii) one or more axially and sideways offset auxiliary lightguiding cores for selectively receiving the return light from different imaging depths.

15. An optical system as claimed in claim 11, comprising a quasi-ellipsoidal optical window with a surface shape selected to be parallel to a scanning surface of an apex of the lens group, whereby a relative geometry of the lens group, an instantaneously optically active region of the optical window and the point observational field on a distal side of the optical window remains invariant throughout an image acquisition portion of a scan.

16. A lens surface quality assessment method, comprising:
   positioning a known diameter pinhole at a focus of an optical system as claimed in claim 11;
   optically driving the optical waveguide;
   measuring a power transmitted through the pinhole;
   removing the pinhole and measuring a total output power; and
   determining a measure of a root mean square surface roughness of the lens from a ratio of the power through pinhole to the total power.

17. An in-vivo, one or many-photon descanned fluorescence imaging system comprising the optical system of claim 11.

18. An active alignment method, comprising:
   mounting an optical waveguide and a lens group as claimed in claim 1 comprising a plurality of lens elements in an alignment jig with an exit tip of the optical waveguide substantially against a proximal surface of the lens group
   optically driving the optical waveguide;
   directing output light from the lens group into an optical detector;
   establishing a least-aberration optimal relative position and orientation by adjusting relative position and orientation of the lens group and the optical waveguide;
   bonding the lens elements or otherwise assembling them into fixed relative position and orientation.

19. An optical system, comprising:
   an optical waveguide having a main core and a highly multimoded secondary core; and
   one or more lens elements, each of uniform refractive index;
   wherein an exit tip of the optical waveguide is located substantially against a proximal surface of a lens group;
   the main core is configured to transmit driving or excitation light from a light source to the lens group;

the lens group is configured to
 i) focus, with high wavefront aberration correction, the driving or excitation light received from the exit tip of the optical waveguide to a point observational field with narrow point spread function beyond a distal surface of the lens group; and
 ii) transmit, with modest aberration correction, fluorescence from the point observational field back to the exit tip of the optical waveguide at the fluorescence wavelength; and the secondary core is configured to receive the fluorescence;

the optical system having resolution and aberration correction criteria such that:

a) the numerical aperture of light focussed by the lens group is greater than or equal to 0.15 when the optical waveguide is driven at a nominal driving wavelength; and b) the Strehl product power:

$$\max_{r \in \mathbb{R}^3} (\mathcal{S}(r, \lambda_D)^N)$$

is greater than or equal to 0.5 for N-photon imaging.

* * * * *